US010499987B2

(12) United States Patent
Germain et al.

(10) Patent No.: US 10,499,987 B2
(45) Date of Patent: Dec. 10, 2019

(54) TISSUE CUTTING SYSTEMS AND METHODS

(71) Applicant: BOSTON SCIENTIFIC SCIMED, INC., Maple Grove, MN (US)

(72) Inventors: Aaron Germain, Campbell, CA (US); John H. Shadduck, Menlo Park, CA (US); Michael D. Walker, San Francisco, CA (US); Kyle Klein, San Jose, CA (US); Csaba Truckai, Saratoga, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 46 days.

(21) Appl. No.: 15/656,386

(22) Filed: Jul. 21, 2017

(65) Prior Publication Data

US 2017/0333127 A1    Nov. 23, 2017

Related U.S. Application Data

(63) Continuation of application No. 13/540,396, filed on Jul. 2, 2012, now Pat. No. 9,737,362.

(Continued)

(51) Int. Cl.
*A61B 18/18* (2006.01)
*A61B 17/32* (2006.01)
(Continued)

(52) U.S. Cl.
CPC ........ *A61B 18/18* (2013.01); *A61B 17/32002* (2013.01); *A61B 18/1482* (2013.01);
(Continued)

(58) Field of Classification Search
CPC ................................ A61B 17/32002
See application file for complete search history.

(56) References Cited

U.S. PATENT DOCUMENTS 4,650,462 A    3/1987   DeSatnick et al.
4,735,603 A    4/1988   Goodson et al.
(Continued)

FOREIGN PATENT DOCUMENTS

EP    2100567 A1    9/2009
GB    2327351 A     1/1999
(Continued)

OTHER PUBLICATIONS

"AAGL Practice Report: Practice Guidelines for the Management of Hysteroscopic Distending Media Replaces Hysteroscopic Fluid Monitoring Guidelines," Journal of Minimally Invasive Gynecology, 20(2): 137-148, 2013.
(Continued)

*Primary Examiner* — Carl H Layno
*Assistant Examiner* — Jennifer L Ghand
(74) *Attorney, Agent, or Firm* — Seager, Tufte & Wickhem, LLP

(57) ABSTRACT

A probe for resecting and coagulating tissue comprises an outer sleeve having a tissue cutting window and an inner sleeve having a tissue cutting distal end. And RF cutting region is formed at the distal end of the inner member and an RF coagulation region is formed on an exterior surface of the inner member immediately proximal to the cutting surface. A single power supply providing a single RF energy mode can be connected to both RF applicator regions to simultaneously cut and coagulate tissue.

11 Claims, 27 Drawing Sheets

Related U.S. Application Data

(60) Provisional application No. 61/505,000, filed on Jul. 6, 2011.

(51) Int. Cl.

| | | |
|---|---|---|
| *A61B 18/14* | (2006.01) | |
| *A61B 18/08* | (2006.01) | |
| *A61B 18/00* | (2006.01) | |
| *A61B 17/42* | (2006.01) | |
| *A61B 1/012* | (2006.01) | |
| *A61B 1/303* | (2006.01) | |

(52) U.S. Cl.
CPC .............. *A61B 1/012* (2013.01); *A61B 1/303* (2013.01); *A61B 18/08* (2013.01); *A61B 2017/320028* (2013.01); *A61B 2017/4216* (2013.01); *A61B 2018/00196* (2013.01); *A61B 2018/00589* (2013.01); *A61B 2018/00601* (2013.01); *A61B 2018/1475* (2013.01); *A61B 2218/002* (2013.01); *A61B 2218/007* (2013.01)

(56) References Cited

U.S. PATENT DOCUMENTS

| | | | |
|---|---|---|---|
| 4,971,034 | A | 11/1990 | Doi et al. |
| 5,098,375 | A | 3/1992 | Baier |
| 5,106,364 | A | 4/1992 | Hayafuji et al. |
| 5,277,696 | A | 1/1994 | Hagen |
| 5,382,229 | A | 1/1995 | Grabenkort et al. |
| 5,437,629 | A | 8/1995 | Goldrath |
| 5,476,447 | A | 12/1995 | Noda et al. |
| 5,643,203 | A | 7/1997 | Beiser et al. |
| 5,669,921 | A | 9/1997 | Berman et al. |
| 5,730,752 | A | 3/1998 | Alden et al. |
| 5,810,858 | A | 9/1998 | Berman et al. |
| 5,823,990 | A | 10/1998 | Henley |
| 5,830,180 | A | 11/1998 | Chandler et al. |
| 5,853,392 | A | 12/1998 | Dennis |
| 5,906,615 | A | 5/1999 | Thompson |
| 5,925,050 | A | 7/1999 | Howard, III |
| 6,032,673 | A | 3/2000 | Savage et al. |
| 6,109,268 | A | 8/2000 | Thapliyal et al. |
| RE36,914 | E | 10/2000 | Carlsen et al. |
| 6,206,014 | B1 | 3/2001 | Cameron, III et al. |
| 6,245,084 | B1 | 6/2001 | Mark et al. |
| 6,358,263 | B2 | 3/2002 | Mark et al. |
| 6,629,986 | B1 | 10/2003 | Ross et al. |
| 7,029,451 | B2 | 4/2006 | Anderson et al. |
| 7,070,604 | B1 | 7/2006 | Garito et al. |
| 7,204,821 | B1 | 4/2007 | Clare et al. |
| 7,226,459 | B2 | 6/2007 | Cesarini et al. |
| 7,384,417 | B2 | 6/2008 | Cucin |
| 7,549,987 | B2 | 6/2009 | Shadduck |
| 7,674,259 | B2 | 3/2010 | Shadduck |
| 7,892,229 | B2 | 2/2011 | Shadduck et al. |
| 8,313,485 | B2 | 11/2012 | Shadduck |
| 8,512,326 | B2 | 8/2013 | Shadduck et al. |
| 8,728,066 | B2 | 5/2014 | Shadduck et al. |
| 9,060,800 | B1* | 6/2015 | Cesarini ........... A61B 17/32002 |
| 2002/0010463 | A1 | 1/2002 | Mulier et al. |
| 2002/0072745 | A1 | 6/2002 | Truckai et al. |
| 2003/0060862 | A1 | 3/2003 | Goble et al. |
| 2004/0049217 | A1 | 3/2004 | Ross et al. |
| 2004/0092980 | A1 | 5/2004 | Cesarini et al. |
| 2004/0102770 | A1 | 5/2004 | Goble |
| 2004/0167427 | A1 | 8/2004 | Quick et al. |
| 2004/0167428 | A1 | 8/2004 | Quick et al. |
| 2004/0267255 | A1 | 12/2004 | Auge, II et al. |
| 2005/0096649 | A1 | 5/2005 | Adams |
| 2005/0236329 | A1 | 10/2005 | Brotherton et al. |
| 2006/0047185 | A1 | 3/2006 | Shener et al. |
| 2006/0135955 | A1 | 6/2006 | Shadduck |
| 2006/0224154 | A1 | 10/2006 | Shadduck et al. |
| 2007/0016182 | A1 | 1/2007 | Lipson et al. |
| 2007/0021713 | A1 | 1/2007 | Kumar et al. |
| 2007/0036768 | A1 | 2/2007 | Fraser et al. |
| 2007/0088275 | A1 | 4/2007 | Stearns et al. |
| 2007/0244353 | A1 | 10/2007 | Larsen |
| 2008/0039832 | A1 | 2/2008 | Palanker et al. |
| 2008/0065060 | A1 | 3/2008 | Ein-Gal |
| 2008/0091061 | A1 | 4/2008 | Kumar et al. |
| 2008/0091071 | A1 | 4/2008 | Kumar et al. |
| 2008/0249553 | A1 | 10/2008 | Gruber et al. |
| 2008/0287893 | A1 | 11/2008 | Ineson |
| 2009/0082715 | A1 | 3/2009 | Charles |
| 2009/0088784 | A1 | 4/2009 | DeBoer et al. |
| 2009/0137943 | A1 | 5/2009 | Stearns et al. |
| 2009/0270898 | A1 | 10/2009 | Chin et al. |
| 2009/0312753 | A1 | 12/2009 | Shadduck |
| 2010/0100091 | A1 | 4/2010 | Truckai |
| 2010/0152533 | A1 | 6/2010 | Mark |
| 2011/0224486 | A1 | 9/2011 | Nguyen et al. |
| 2011/0264090 | A1 | 10/2011 | Shadduck et al. |
| 2011/0306968 | A1 | 12/2011 | Beckman et al. |
| 2012/0053583 | A1 | 3/2012 | Palanker et al. |
| 2012/0271300 | A9 | 10/2012 | Shadduck et al. |
| 2012/0330292 | A1 | 12/2012 | Shadduck et al. |
| 2013/0046304 | A1 | 2/2013 | Germain et al. |
| 2013/0079702 | A1 | 3/2013 | Klein et al. |
| 2013/0103021 | A1 | 4/2013 | Germain et al. |
| 2013/0172805 | A1 | 7/2013 | Truckai et al. |
| 2013/0172870 | A1 | 7/2013 | Germain et al. |
| 2013/0231652 | A1 | 9/2013 | Germain et al. |
| 2013/0296847 | A1 | 11/2013 | Germain et al. |
| 2014/0324065 | A1* | 10/2014 | Bek ........................ A61B 50/13 606/110 |

FOREIGN PATENT DOCUMENTS

| | | |
|---|---|---|
| WO | 2005037088 A2 | 4/2005 |
| WO | 2010096139 A2 | 8/2010 |
| WO | 2010096139 A3 | 8/2010 |
| WO | 2011060189 A1 | 5/2011 |

OTHER PUBLICATIONS

Liu et al., "Clinical Application of Hysteroscopic Electroresection in 775 Cases," J. First Mil. Med. Univ., (in Chinese with English Abstract), 24(4): 467-469, 2004.

Phillips et al., "The Effect of Dilute Vasopressin Solution on Blood Loss During Operative Hysteroscopy," J. Am. Assoc. Gynecol. Laparosc., (Abstract only), 3(4): S38, 1996.

\* cited by examiner

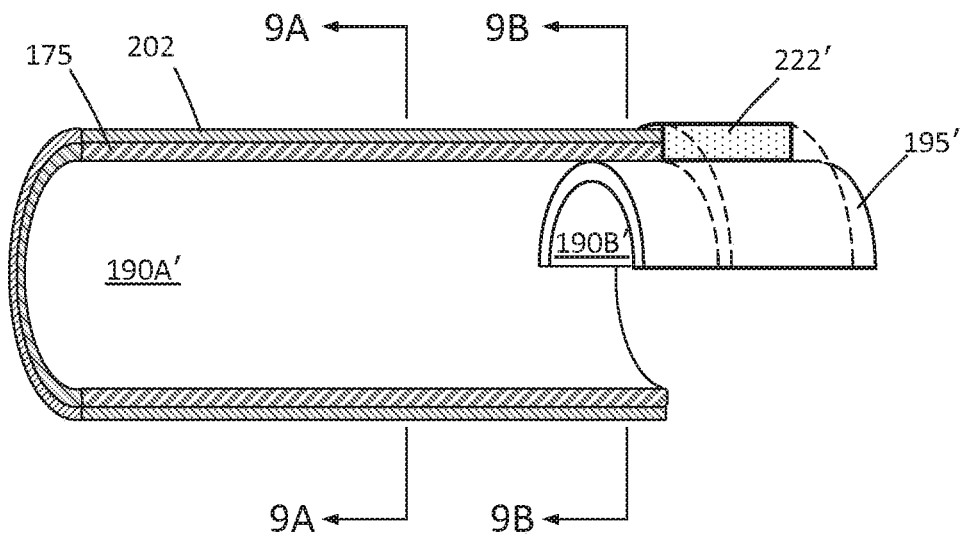
FIG. 8
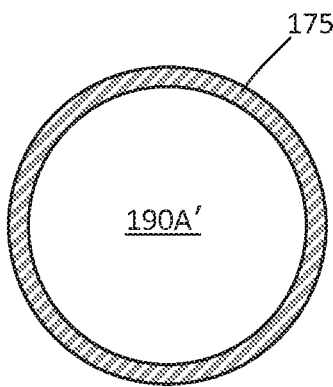 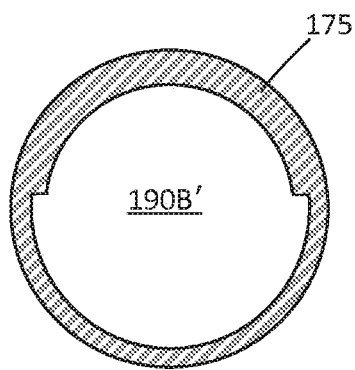
FIG. 9A    FIG. 9B

TISSUE CUTTING SYSTEMS AND METHODS

CROSS REFERENCE TO RELATED APPLICATIONS

This application is a continuation of pending U.S. application Ser. No. 13/540,396, filed Jul. 2, 2012, now U.S. Pat. No. 9,737,362, which claims the benefit of U.S. Provisional Application No. 61/505,000, filed on Jul. 6, 2011, the full disclosures of which are incorporated herein by reference.

FIELD OF THE INVENTION

The present invention relates to systems and methods for example for use cutting and extraction of uterine fibroid tissue, polyps and other abnormal uterine tissue.

BACKGROUND OF THE INVENTION

Uterine fibroids are non-cancerous tumors that develop in the wall of uterus. Such fibroids occur in a large percentage of the female population, with some studies indicating up to 40 percent of all women have fibroids. Uterine fibroids can grow over time to be several centimeters in diameter and symptoms can include menorrhagia, reproductive dysfunction, pelvic pressure and pain.

One current treatment of fibroids is hysteroscopic resection or myomectomy which involves transcervical access to the uterus with a hysteroscope together with insertion of a cutting instrument through a working channel in the hysteroscope. The cutting instrument may be a mechanical tissue cutter or an electrosurgical resection device such as a cutting loop. Mechanical cutting devices are disclosed in U.S. Pat. Nos. 7,226,459; 6,032,673 and 5,730,752 and U.S. Published Patent Application 2009/0270898. An electrosurgical cutting device is disclosed in U.S. Pat. No. 5,906,615.

As with many surgical resections, fibroid resection can cause bleeding which may in some cases require cauterization. Usually, cauterization would require exchange of the cutting instrument with a cauterization tool in the working channel of the hysterocope. Cauterization might also require use of a different electrosurgical power supply which is capable of delivering a coagulation current which is usually different than the cutting current utilized by the cutting instrument. The need to exchange tools and often power supplies as well can increase the treatment time and complexity.

For these reasons, it would be desirable to provide improved tissue resection apparatus, systems, and methods, particularly for use in resecting fibroids through the working channel of a hysterocope, where both cutting an coagulation could be performed using the same cutting tool and where a single power supply could be used to provide both cutting and coagulation power to the cutting tool. At least some of these objectives will be met by the inventions described below.

SUMMARY OF THE INVENTION

The present invention provides apparatus, systems, and methods for resecting tissue with the ability to coagulate the resected tissue without having to exchange tools or power supplies. The apparatus, systems, and methods of the present invention are particularly advantageous since both resection (cutting) and coagulation can be performed using the same tool and the same power supply. Additionally, the present invention allows for substantially simultaneous coagulation of the just cut tissue using a single mode of radio frequency (RF) power from the same power supply. In this way, the need to switch between a cutting current and a coagulation current is avoided.

In the first aspect, a tissue cutting system comprises a probe and a power supply. The probe includes a windowed outer sleeve and a reciprocating inner cutting sleeve, where the inner cutting sleeve reciprocates between a window-opened and a window-closed configuration. The cutting sleeve is configured with first and second discreet RF applicator regions, where both regions are adapted to be coupled to a single RF source which usually operates in a single RF mode (current characteristic). The system further includes an RF source adapted to coupled to the probe such that a single mode of RF energy is delivered to both the first and second RF applicator regions. The RF energy delivered to the first RF applicator region allows the distal end of the inner member to cut tissue as the inner member is advanced past the cutting window. The RF energy delivered to the second RF applicator region will contact tissue that has just been cut by the first applicator region, wherein the cut tissue is coagulated.

The first RF applicator region is typically a cutting electrode, such as a ring electrode mounted coaxially at the distal end of the inner cutting member. The first RF applicator could be arranged as a bipolar electrode, but will more typically be formed as a monopolar electrode which will be arranged with a second polarity electrode, typically having a much larger surface area, where the second polarity electrode can be on the probe or could be a conventional dispersive electrode placed on the patient's skin typically on the lower back.

The second RF applicator region may comprise of a variety of configurations. For example, the second RF applicator region could be an electrode disposed on an outer surface of the inner cutting sleeve covered by a thin wall dielecpric material so that the coagulation energy is delivered by capacitive coupling. Alternatively, the second RF applicator region could comprise a pair of spaced-apart bipolar electrodes, e.g. a pair of ring electrodes which are axially spaced apart. Still further alternatively, the second RF applicator region could comprise a resistive element or region to provide for resistance heating. Further alternatively, the RF applicator region could comprise a positive temperature coefficient resistive (PTCR) material to provide an inherently temperature-controlled resistive heater element.

While the first RF applicator region and the second RF applicator region may take a variety of specific forms, their arrangement on the apparatus will usually be the same, where the first RF applicator region is at distal end or tip of the inner cutting sleeve to allow for tissue cutting or resection as the inner cutting sleeve is advanced. The second RF applicator region will usually be disposed on an exterior surface of the inner sleeve at a location immediately proximal to the first RF applicator region. Placement of the second RF applicator region in such close proximity to the first RF applicator region allows for transfer of coagulation energy to the treated tissue immediately after that tissue has been resected. This allows for coagulation virtually immediately after the tissue has been cut, thus eliminating or at least substantially reducing any bleeding which might occur.

In other aspects of the apparatus of the present invention, the cutting window and the outer sleeve may be partially or fully circumscribed by a dielectric material, where the dielectric material may comprise one or more of a ceramic, a glass, a polymer, or the like.

In yet another optional aspect of the apparatus of the present invention, at least one surface of the outer sleeve proximate the cutting window comprises of material having a comparative tracking index value ranging from 200 volts to 800 volts.

In yet another optional aspect of the apparatus of the present invention, the outer sleeve may have distal tip configured to cut or penetrate tissue. The cutting tip may be a simple sharpen, honed, tapered or otherwise shaped tip which facilitates tissue penetration. Alternatively or additionally, the distal tip of the outer sleeve may have an electrode or other energy transfer surface for delivering RF energy, typically from the same power supply used for the reciprocating inner cutting sleeve, to enhance tissue penetration. Optionally, the cutting tip may be retractable.

In other alternative embodiments, the tissue cutting probe of the present invention includes a handle carrying a motor drive for reciprocating and/or rotating the cutting sleeve. The probe or system still further include a negative pressure (vacuum) source which is connectable to a tissue extraction channel in the inner sleeve. Applying a negative pressure to the extraction channel facilitates removing resected tissue, and the extraction channel may extend through the handle and may include a heat exchanger configured to cool extracted fluids to cool the motor and/or the handle.

In a second aspect of the present invention, methods for resecting tissue comprises interfacing an electrical surgical probe with tissue targeted for resection, such as fibroid tissue within a uterus. The probe comprises a cutting member configured to simultaneously apply a first RF induced energy and second RF induced energy to the tissue utilizing a single RF power load. The probe may moved relative to tissue such that a leading portion or edge of the cutting number applies the first RF-induced energy to tissue for vaporization and cutting of the tissue and a proximal portion or region of the cutting member applies the second RF-induced energy level in order to coagulate the tissue which has been cut by the first energy level. The probes utilized in these methods may be and any of the probes described here and above.

In an alternative method according to the present invention, an electric or electrosurgical probe is interfaced with tissue targeted for resection, where the probe comprises a windowed outer sleeve and a reciprocating and/or cutting sleeve. First and second RF applicator regions may be coupled to a single RF source. The inner sleeve is reciprocated within the outer sleeve for cutting tissue intruding within the window. While the inner sleeve is being reciprocated to cut tissue, the single RF power supply delivers a single RF energy mode simultaneously to both the first and second applicator region. Energy delivered to the first applicator region assists in cutting the tissue while the energy delivered to the second RF applicator region forms a non-ablative non-plasma energy for coagulating tissue which has just been cut by the first applicator region. Other aspects of the methods and apparatus used for performing the methods have been describe above.

BRIEF DESCRIPTION OF DRAWINGS

FIG. 8 is a schematic view of a distal end portion of another embodiment of inner RF cutting sleeve.

FIG. 9A is a cross sectional view of the RF cutting sleeve of FIG. 8 taken along line 9A-9A of FIG. 8.

FIG. 9B is a cross sectional view of the RF cutting sleeve of FIG. 8 taken along line 9B-9B of FIG. 8.

DETAILED DESCRIPTION

Figure 1:
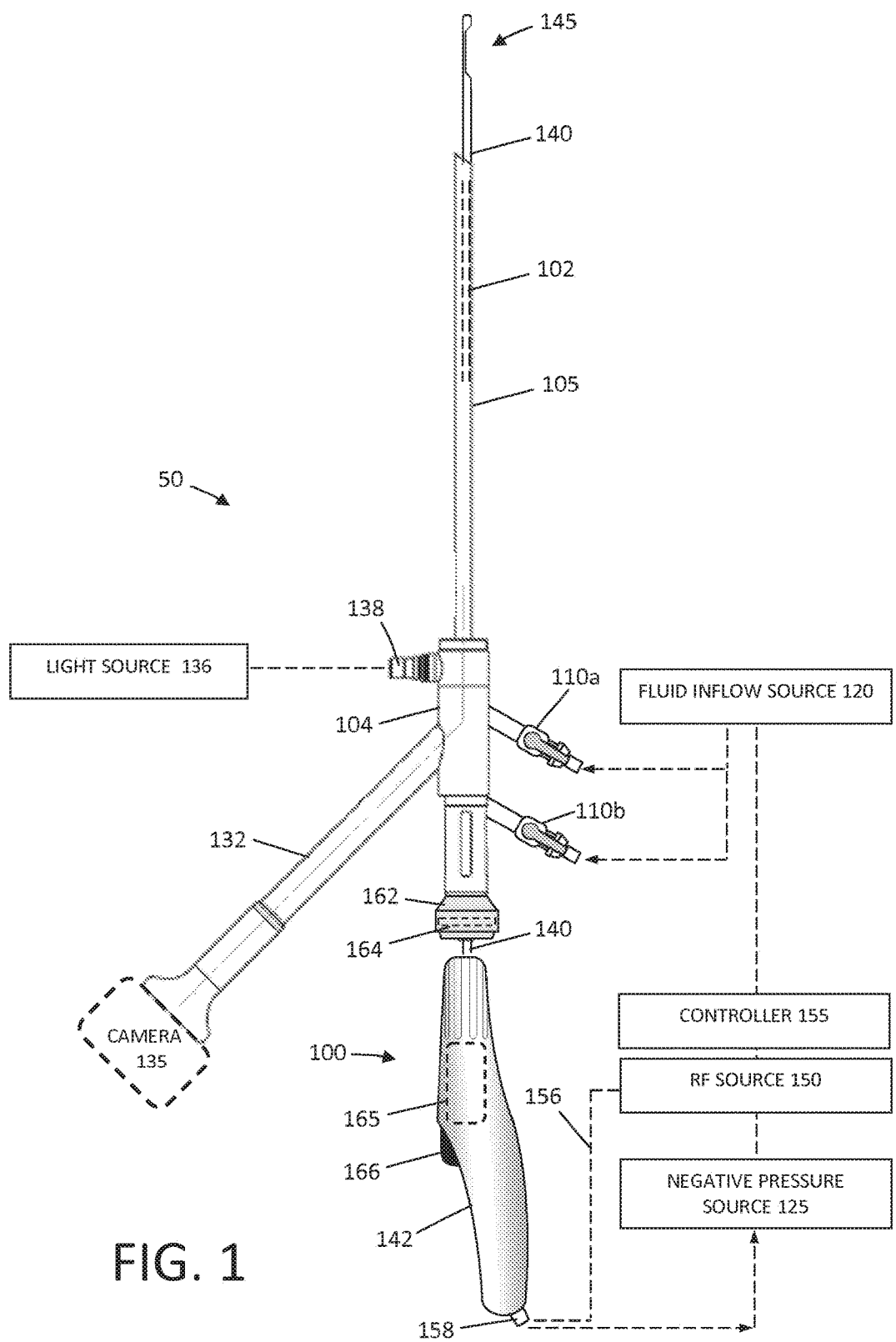
FIG. 1 is a plan view of an assembly including a hysteroscope and a tissue-cutting device corresponding to the invention that is inserted through the working channel of the hysteroscope.
Figure 2:
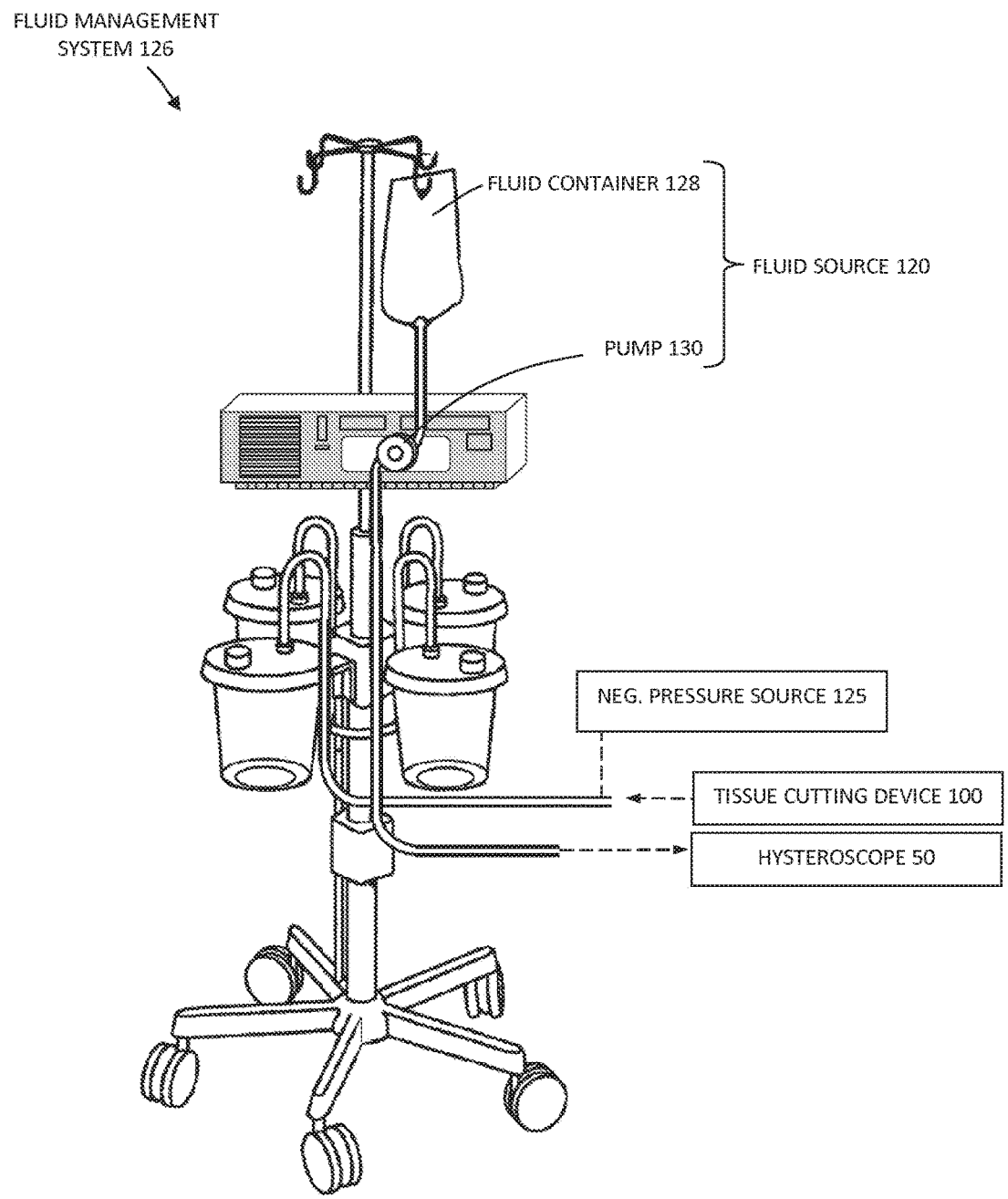
FIG. 2 is a schematic perspective view of a fluid management system used for distending the uterus and for assisting in electrosurgical tissue cutting and extraction.
Figure 3:
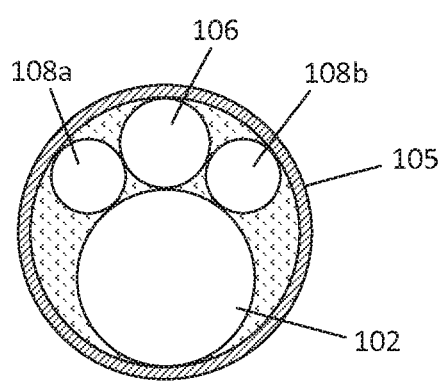
FIG. 3 is a cross-sectional view of the shaft of the hysteroscope of FIG. 1 showing various channels therein.

FIG. 1 illustrates an assembly that comprises an endoscope 50 used for hysteroscopy together with a tissue-extraction device 100 extending through a working channel 102 of the endoscope. The endoscope or hysteroscope 50 has a handle 104 coupled to an elongated shaft 105 having a diameter of 5 mm to 7 mm. The working channel 102 therein may be round, D-shaped or any other suitable shape. The endoscope shaft 105 is further configured with an optics channel 106 and one or more fluid inflow/outflow channels 108a, 108b (FIG. 3) that communicate with valve-connectors 110a, 110b configured for coupling to a fluid inflow source 120 thereto, or optionally a negative pressure source 125 (FIGS. 1-2). The fluid inflow source 120 is a component of a fluid management system 126 as is known in the art (FIG. 2) which comprises a fluid container 128 and pump mechanism 130 which pumps fluid through the hysteroscope 50 into the uterine cavity. As can be seen in FIG. 2, the fluid management system 126 further includes the negative pressure source 125 (which can comprise an operating room wall suction source) coupled to the tissue-cutting device 100. The handle 104 of the endoscope includes the angled extension portion 132 with optics to which a videoscopic camera 135 can be operatively coupled. A light source 136 also is coupled to light coupling 138 on the handle of the hyteroscope 50. The working channel 102 of the hysteroscope is configured for insertion and manipulation of the tissue-cutting and extracting device 100, for example to treat and remove fibroid tissue. In one embodiment, the hysteroscope shaft 105 has an axial length of 21 cm, and can comprise a 0° scope, or 15° to 30° scope.

Still referring to FIG. 1, the tissue-cutting device 100 has a highly elongated shaft assembly 140 configured to extend through the working channel 102 in the hysteroscope. A handle 142 of the tissue-cutting device 100 is adapted for manipulating the electrosurgical working end 145 of the device. In use, the handle 142 can be manipulated both rotationally and axially, for example, to orient the working end 145 to cut targeted fibroid tissue. The tissue-cutting device 100 has subsystems coupled to its handle 142 to enable electrosurgical cutting of targeted tissue. A radiofrequency generator or RF source 150 and controller 155 are coupled to at least one RF electrode carried by the working end 145 as will be described in detail below. In one embodiment shown in FIG. 1, an electrical cable 156 and negative pressure source 125 are operatively coupled to a connector 158 in handle 142. The electrical cable couples the RF source 150 to the electrosurgical working end 145. The negative pressure source 125 communicates with a tissue-extraction channel 160 in the shaft assembly 140 of the tissue extraction device 100 (FIG. 4).

FIG. 1 further illustrates a seal housing 162 that carries a flexible seal 164 carried by the hysteroscope handle 104 for sealing the shaft 140 of the tissue-cutting device 100 in the working channel 102 to prevent distending fluid from escaping from a uterine cavity.

In one embodiment as shown in FIG. 1, the handle 142 of tissue-cutting device 100 includes a motor drive 165 for reciprocating or otherwise moving a cutting component of the electrosurgical working end 145 as will be described below. The handle 142 optionally includes one or more actuator buttons 166 for actuating the device. In another embodiment, a footswitch can be used to operate the device. In one embodiment, the system includes a switch or control mechanism to provide a plurality of reciprocation speeds, for example 1 Hz, 2 Hz, 3 Hz, 4 Hz and up to 8 Hz. Further, the system can include a mechanism for moving and locking the reciprocating cutting sleeve in a non-extended position and in an extended position. Further, the system can include a mechanism for actuating a single reciprocating stroke.

Figure 4:
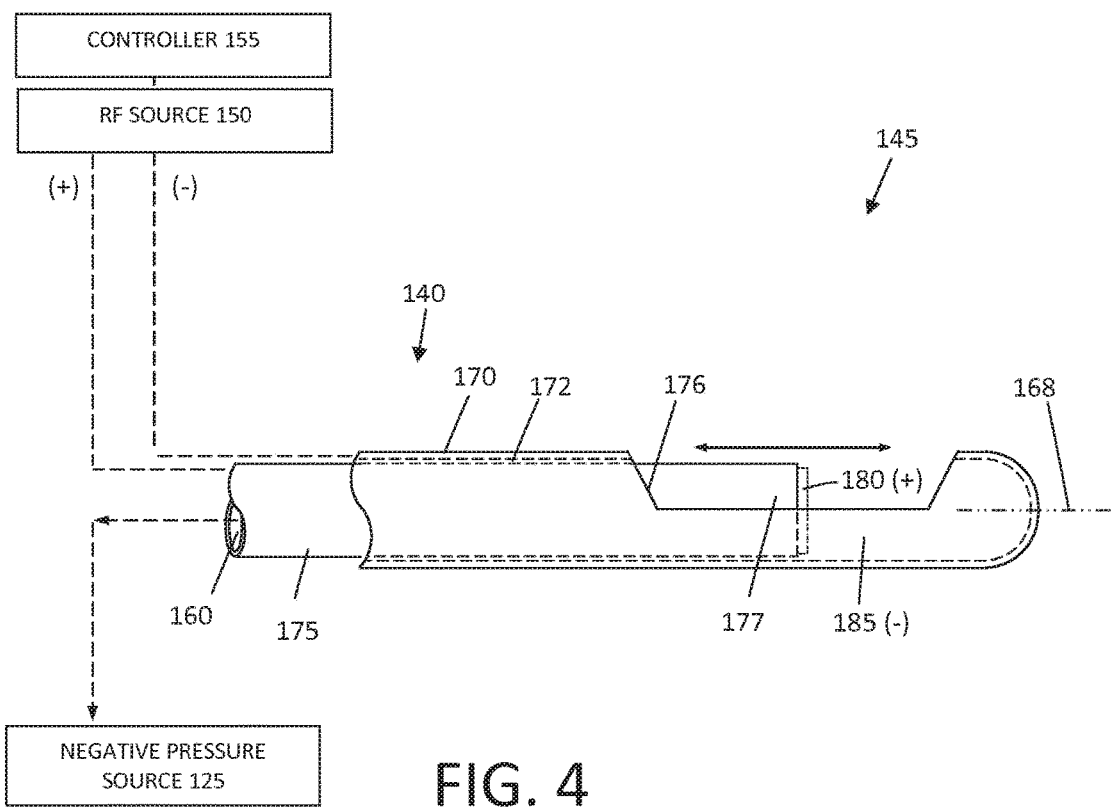
FIG. 4 is a schematic side view of the working end of the electrosurgical tissue-cutting device of FIG. 1 showing an outer sleeve and a reciprocating inner sleeve and an electrode arrangement.

Referring to FIGS. 1 and 4, an electrosurgical tissue-cutting device has an elongate shaft assembly 140 extending about longitudinal axis 168 comprising an exterior or first outer sleeve 170 with passageway or lumen 172 therein that accommodates a second or inner sleeve 175 that can reciprocate (and optionally rotate or oscillate) in lumen 172 to cut tissue as is known in that art of such tubular cutters. In one embodiment, the tissue-receiving window 176 in the outer sleeve 170 has an axial length ranging between 10 mm and 30 mm and extends in a radial angle about outer sleeve 170 from about 45° to 210° relative to axis 168 of the sleeve. The outer and inner sleeves 170 and 175 can comprise a thin-wall stainless steel material and function as opposing polarity electrodes as will be described in detail below. FIGS. 6A-8 illustrate insulative layers carried by the outer and inner sleeves 170 and 175 to limits, control and/or prevent unwanted electrical current flows between certain portions go the sleeve. In one embodiment, a stainless steel outer sleeve 170 has an O.D. of 0.143" with an I.D. of 0.133" and with an inner insulative layer (described below) the sleeve has a nominal I.D. of 0.125". In this embodiment, the stainless steel inner sleeve 175 has an O.D. of 0.120" with an I.D. of 0.112". The inner sleeve 175 with an outer insulative layer has a nominal O.D. of about 0.123" to 0.124" to reciprocate in lumen 172. In other embodiments, outer and or inner sleeves can be fabricated of metal, plastic, ceramic of a combination thereof. The cross-section of the sleeves can be round, oval or any other suitable shape.

As can be seen in FIG. 4, the distal end 177 of inner sleeve 175 comprises a first polarity electrode with distal cutting electrode edge 180 about which plasma can be generated. The electrode edge 180 also can be described as an active electrode during tissue cutting since the electrode edge 180 then has a substantially smaller surface area than the opposing polarity or return electrode. In one embodiment in FIG. 4, the exposed surfaces of outer sleeve 170 comprises the second polarity electrode 185, which thus can be described as the return electrode since during use such an electrode surface has a substantially larger surface area compared to the functionally exposed surface area of the active electrode edge 180.

Figure 5:
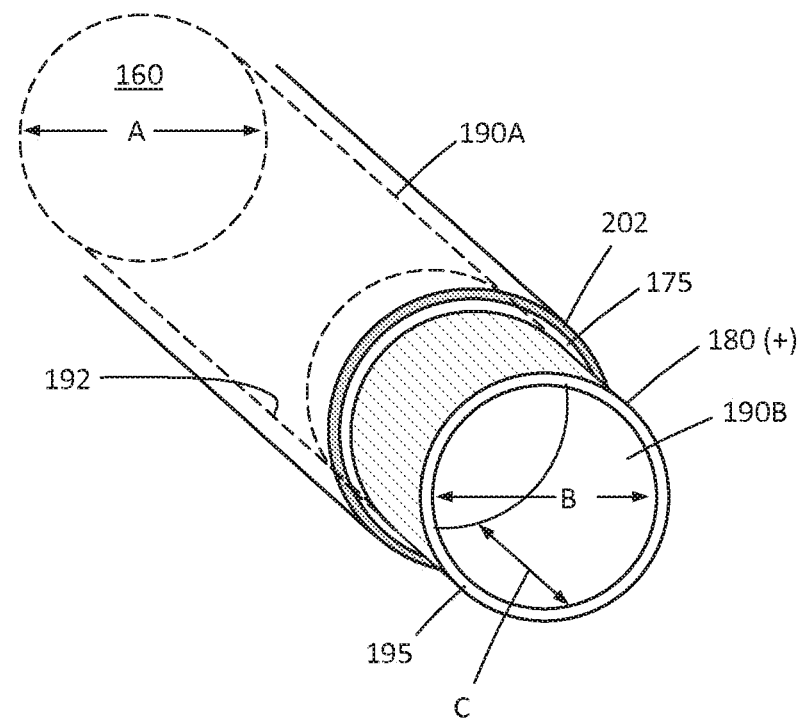
FIG. 5 is a schematic perspective view of the working end of the inner sleeve of FIG. 4 showing its electrode edge.
Figure 6A:
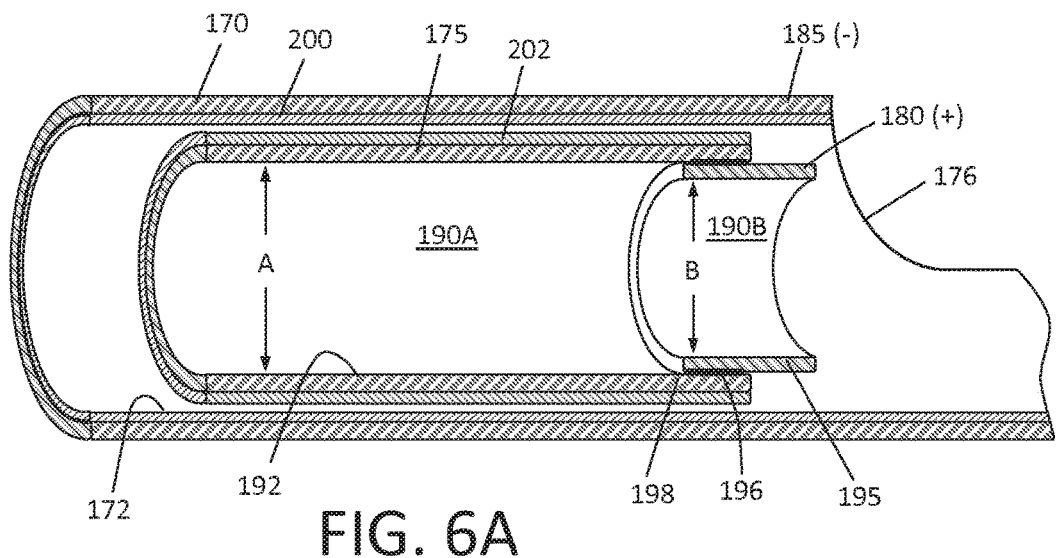
FIG. 6A is a schematic cut-away view of a portion of outer sleeve, inner RF cutting sleeve and a tissue-receiving window of the outer sleeve.

In one aspect of the invention, the inner sleeve or cutting sleeve 175 has an interior tissue extraction lumen 160 with first and second interior diameters that are adapted to electrosurgically cut tissue volumes rapidly—and thereafter consistently extract the cut tissue strips through the highly elongated lumen 160 without clogging. Now referring to FIGS. 5 and 6A, it can be seen that the inner sleeve 175 has a first diameter portion 190A that extends from the handle 142 (FIG. 1) to a distal region 192 of the sleeve 175 wherein the tissue extraction lumen transitions to a smaller second diameter lumen 190B with a reduced diameter indicated at B which is defined by the electrode sleeve element 195 that provides cutting electrode edge 180. The axial length C of the reduced cross-section lumen 190B can range from about 2 mm to 20 mm. In one embodiment, the first diameter A is 0.112" and the second reduced diameter B is 0.100". As shown in FIG. 5, the inner sleeve 175 can be an electrically conductive stainless steel and the reduced diameter electrode portion also can comprise a stainless steel electrode sleeve element 195 that is welded in place by weld 196 (FIG. 6A). In another alternative embodiment, the electrode and reduced diameter electrode sleeve element 195 comprises a tungsten tube that can be press fit into the distal end 198 of inner sleeve 175. FIGS. 5 and 6A further illustrates the interfacing insulation layers 202 and 204 carried by the first and second sleeves 170, 175, respectively. In FIG. 6A, the outer sleeve 170 is lined with a thin-wall insulative material 200, such as PFA, or another material described below. Similarly, the inner sleeve 175 has an exterior insulative layer 202. These coating materials can be lubricious as well as electrically insulative to reduce friction during reciprocation of the inner sleeve 175.

The insulative layers 200 and 202 described above can comprise a lubricious, hydrophobic or hydrophilic polymeric material. For example, the material can comprise a bio-compatible material such as PFA, TEFLON®, polytetrafluroethylene (PTFE), FEP (Fluorinated ethylenepropylene), polyethylene, polyamide, ECTFE (Ethylenechlorotri-fluoro-ethylene), ETFE, PVDF, polyvinyl chloride or silicone.

Figure 6B:
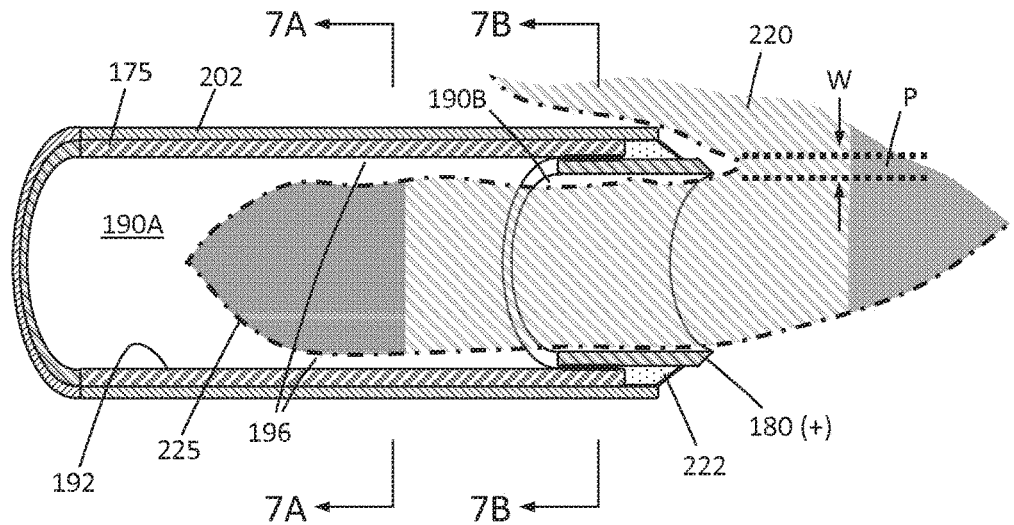
FIG. 6B is a schematic view of a distal end portion another embodiment of inner RF cutting sleeve.

Now turning to FIG. 6B, another variation of inner sleeve 175 is illustrated in a schematic view together with a tissue volume being resected with the plasma electrode edge 180. In this embodiment, as in other embodiments in this disclosure, the RF source operates at selected operational parameters to create a plasma around the electrode edge 180 of electrode sleeve 195 as is known in the art. Thus, the plasma generated at electrode edge 180 can cut and ablate a path P in the tissue 220, and is suited for cutting fibroid tissue and other abnormal uterine tissue. In FIG. 6B, the distal portion of the cutting sleeve 175 includes a ceramic collar 222 which is adjacent the distal edge 180 of the electrode sleeve 195. The ceramic 222 collar functions to confine plasma formation about the distal electrode edge 180 and functions further to prevent plasma from contacting and damaging the polymer insulative layer 202 on the cutting sleeve 175 during operation. In one aspect of the invention, the path P cut in the tissue 220 with the plasma at electrode edge 180 provides a path P having an ablated width indicated at W, wherein such path width W is substantially wide due to tissue vaporization. This removal and vaporization of tissue in path P is substantially different than the effect of cutting similar tissue with a sharp blade edge, as in various prior art devices. A sharp blade edge can divide tissue (without cauterization) but applies mechanical force to the tissue and may prevent a large cross section slug of tissue from being cut. In contrast, the plasma at the electrode edge 180 can vaporize a path P in tissue without applying any substantial force on the tissue to thus cut larger cross sections or slugs strips of tissue. Further, the plasma cutting effect reduces the cross section of tissue strip 225 received in the tissue-extraction lumen 190B. FIG. 6B depicts a tissue strip to 225 entering lumen 190B which has such a smaller cross-section than the lumen due to the vaporization of tissue. Further, the cross section of tissue 225 as it enters the larger cross-section lumen 190A results in even greater free space 196 around the tissue strip 225. Thus, the resection of tissue with the plasma electrode edge 180, together with the lumen transition from the smaller cross-section (190B) to the larger cross-section (190A) of the tissue-extraction lumen 160 can significantly reduce or eliminate the potential for successive resected tissue strips 225 to clog the lumen. Prior art resection devices with such small diameter tissue-extraction lumen typically have problems with tissue clogging.

In another aspect of the invention, the negative pressure source 225 coupled to the proximal end of tissue-extraction lumen 160 (see FIGS. 1 and 4) also assists in aspirating and moving tissue strips 225 in the proximal direction to a collection reservoir (not shown) outside the handle 142 of the device.

Figure 7A:
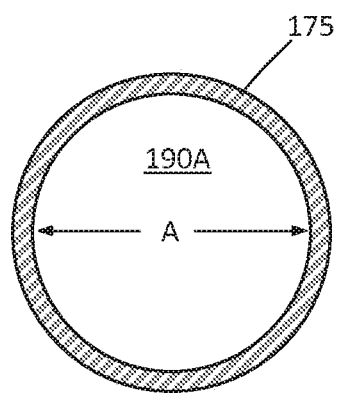
FIG. 7A is a cross sectional view of the inner RF cutting sleeve of FIG. 6B taken along line 7A-7A of FIG. 6B.
Figure 7B:
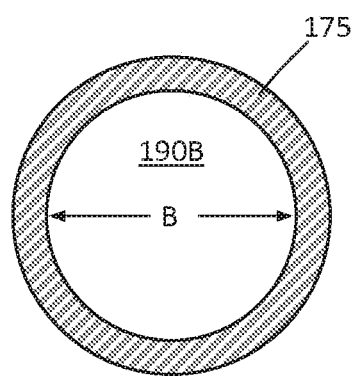
FIG. 7B is another cross sectional view of the inner RF cutting sleeve of FIG. 6B taken along line 7B-7B of FIG. 6B.

FIGS. 7A-7B illustrate the change in lumen diameter of cutting sleeve 175 of FIG. 6B. FIG. 8 illustrates the distal end of a variation of cutting sleeve 175' which is configured with an electrode cutting element 195' that is partially tubular in contrast to the previously described tubular electrode element 195 (FIGS. 5 and 6A). FIGS. 9A-9B again illustrate the change in cross-section of the tissue-extraction lumen between reduced cross-section region 190B' and the increased cross-section region 190A' of the cutting sleeve 175' of FIG. 8. Thus, the functionality remains the same whether the cutting electrode element 195' is tubular or partly tubular. In FIG. 8A, the ceramic collar 222' is shown, in one variation, as extending only partially around sleeve 175 to cooperate with the radial angle of cutting electrode element 195'. Further, the variation of FIG. 8 illustrates that the ceramic collar 222' has a larger outside diameter than insulative layer 202. Thus, friction may be reduced since the short axial length of the ceramic collar 222' interfaces and slides against the interfacing insulative layer 200 about the inner surface of lumen 172 of outer sleeve 170.

In general, one aspect of the invention comprises a tissue cutting and extracting device (FIGS. 10A-11C) that includes first and second concentric sleeves having an axis and wherein the second (inner) sleeve 175 has an axially-extending tissue-extraction lumen therein, and wherein the second sleeve 175 is moveable between axially non-extended and extended positions relative to a tissue-receiving window 176 in first sleeve 170 to resect tissue, and wherein the tissue extraction lumen 160 has first and second cross-sections. The second sleeve 175 has a distal end configured as a plasma electrode edge 180 to resect tissue disposed in tissue-receiving window 176 of the first sleeve 170. Further, the distal end of the second sleeve, and more particularly, the electrode edge 180 is configured for plasma ablation of a substantially wide path in the tissue. In general, the tissue-extraction device is configured with a tissue extraction lumen 160 having a distal end portion with a reduced cross-section that is smaller than a cross-section of medial and proximal portions of the lumen 160.

In one aspect of the invention, referring to FIGS. 7A-7B and 9A-9B, the tissue-extraction lumen 160 has a reduced cross-sectional area in lumen region 190A proximate the plasma cutting tip or electrode edge 180 wherein said reduced cross section is less that 95%, 90%, 85% or 80% than the cross sectional area of medial and proximal portions 190B of the tissue-extraction lumen, and wherein the axial length of the tissue-extraction lumen is at least 10 cm, 20 cm, 30 cm or 40 cm. In one embodiment of tissue-cutting device 100 for hysteroscopic fibroid cutting and extraction (FIG. 1), the shaft assembly 140 of the tissue-cutting device is 35 cm in length.

Figure 10A:
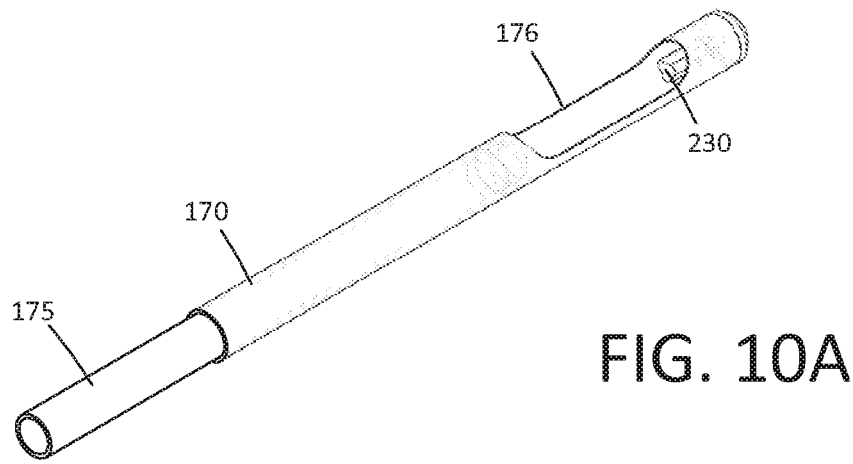
FIG. 10A is a perspective view of the working end of the tissue-cutting device of FIG. 1 with the reciprocating RF cutting sleeve in a non-extended position.
Figure 10B:
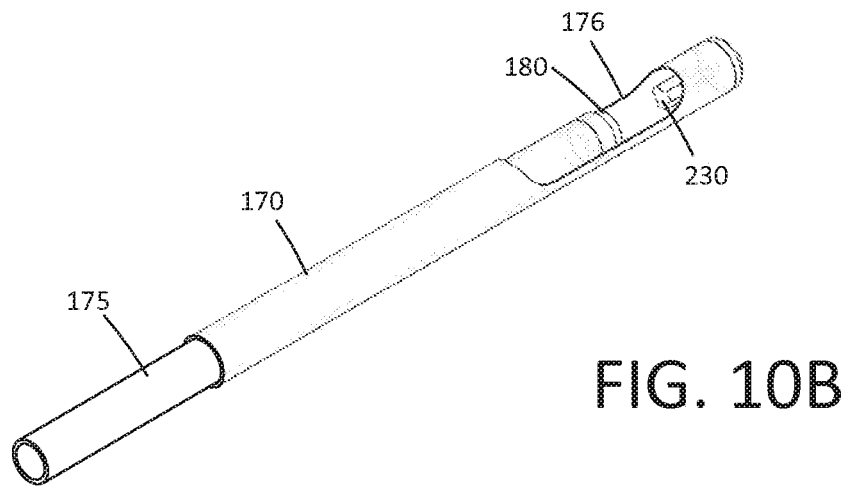
FIG. 10B is a perspective view of the tissue-cutting device of FIG. 1 with the reciprocating RF cutting sleeve in a partially extended position.
Figure 10C:
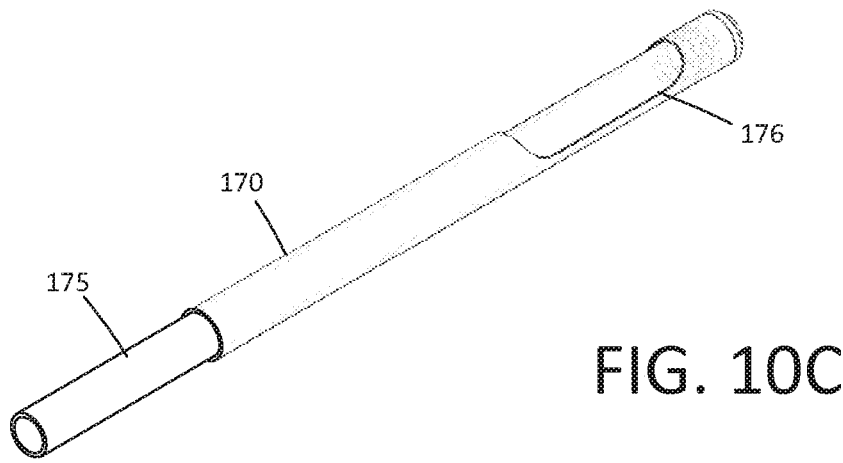
FIG. 10C is a perspective view of the tissue-cutting device of FIG. 1 with the reciprocating RF cutting sleeve in a fully extended position across the tissue-receiving window.
Figure 11A:
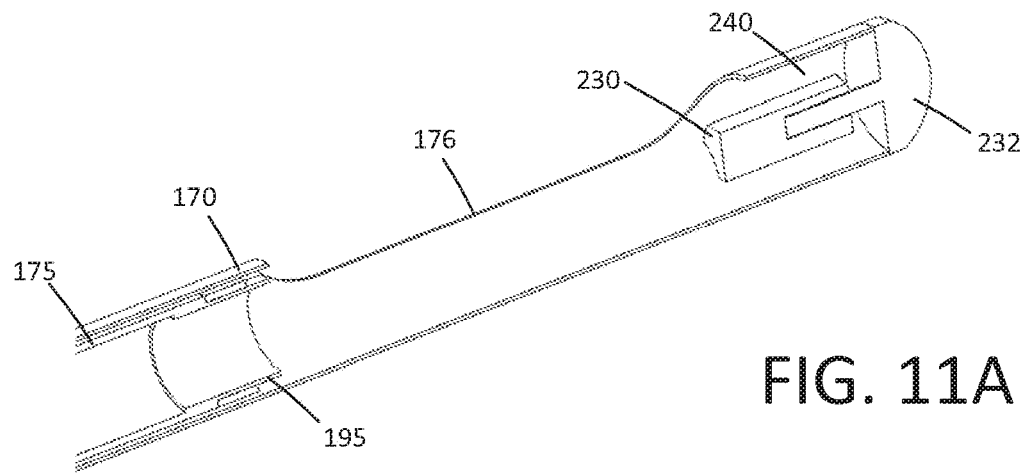
FIG. 11A is a sectional view of the working end of the tissue-cutting device of FIG. 10A with the reciprocating RF cutting sleeve in a non-extended position.
Figure 11B:
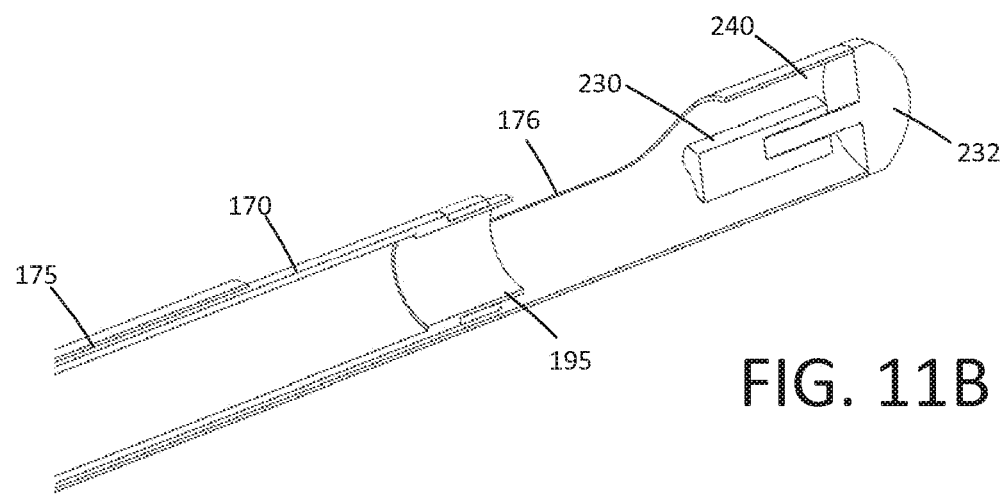
FIG. 11B is a sectional view of the working end of FIG. 10B with the reciprocating RF cutting sleeve in a partially extended position.
Figure 11C:
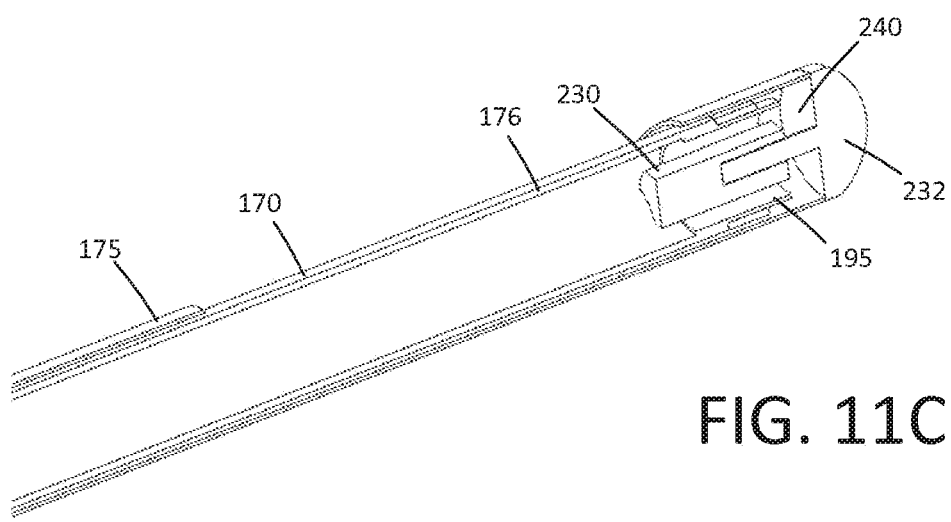
FIG. 11C is a sectional view of the working end of FIG. 10C with the reciprocating RF cutting sleeve in a fully extended position.

FIGS. 10A-10C illustrate the working end 145 of the tissue-cutting device 100 with the reciprocating cutting sleeve or inner sleeve 175 in three different axial positions relative to the tissue receiving window 176 in outer sleeve 170. In FIG. 10A, the cutting sleeve 175 is shown in a retracted or non-extended position in which the sleeve 175 is at it proximal limit of motion and is prepared to advance distally to an extended position to thereby electrosurgically cut tissue positioned in and/or suctioned into in window 176. FIG. 10B shows the cutting sleeve 175 moved and advanced distally to a partially advanced or medial position relative to tissue cutting window 176. FIG. 10C illustrates the cutting sleeve 175 fully advanced and extended to the distal limit of its motion wherein the plasma cutting electrode 180 has extended past the distal end 226 of tissue-receiving window 176 at which moment the resected tissue strip 225 in excised from tissue volume 220 and captured in reduced cross-sectional lumen region 190A.

Now referring to FIGS. 10A-10C and FIGS. 11A-11C, another aspect of the invention comprises "tissue displacement" mechanisms provided by multiple elements and processes to "displace" and move tissue strips 225 in the proximal direction in lumen 160 of cutting sleeve 175 to thus ensure that tissue does not clog the lumen of the inner sleeve 175. As can be seen in FIG. 10A and the enlarged views of FIGS. 11A-11C, one tissue displacement mechanism comprises a projecting element 230 that extends proximally from distal tip 232 which is fixedly attached to outer sleeve 170. The projecting element 230 extends proximally along central axis 168 in a distal chamber 240 defined by outer sleeve 170 and distal tip 232. In one embodiment depicted in FIG. 11A, the shaft-like projecting element 230, in a first functional aspect, comprises a mechanical pusher that functions to push a captured tissue strip 225 proximally from the small cross-section lumen 190B of cutting sleeve 175 as the cutting sleeve 175 moves to its fully advanced or extended position. In a second functional aspect, the chamber 240 in the distal end of sleeve 170 is configured to capture a volume of saline distending fluid 244 from the working space, and wherein the existing RF electrodes of the working end 145 are further configured to explosively vaporize the captured fluid 244 to generate proximally-directed forces on tissue strips 225 resected and disposed in lumen 160 of the cutting sleeve 175. Both of these two functional elements and processes (tissue displacement mechanisms) can apply a substantial mechanical force on the captured tissue strips 225 by means of the explosive vaporization of liquid in chamber 240 and can function to move tissue strips 225 in the proximal direction in the tissue-extraction lumen 160. It has been found that using the combination of multiple functional elements and processes can virtually eliminate the potential for tissue clogging the tissue extraction lumen 160.

Figure 12A:
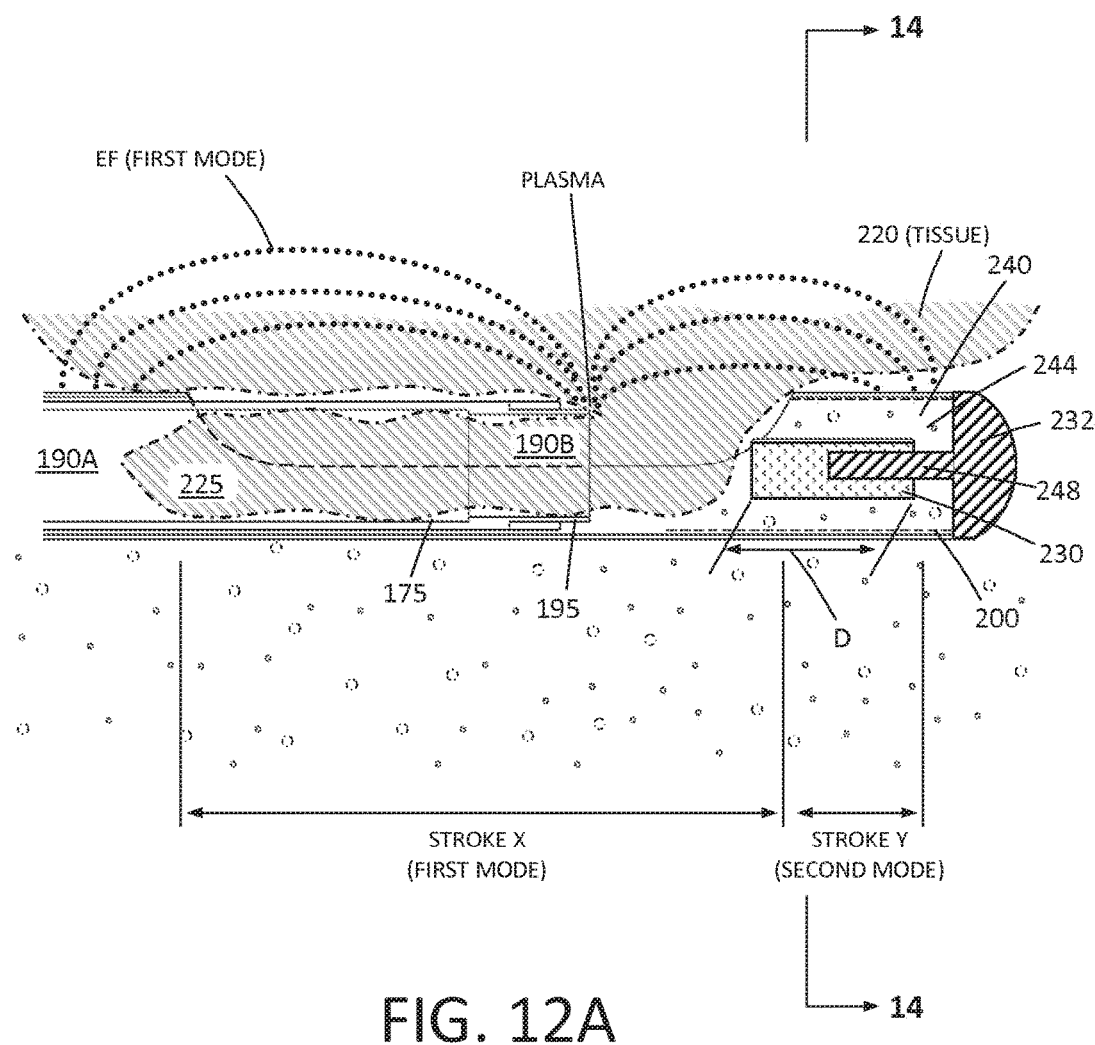
FIG. 12A is an enlarged sectional view of the working end of tissue-cutting device of FIG. 11B with the reciprocating RF cutting sleeve in a partially extended position showing the RF field in a first RF mode and plasma cutting of tissue.
Figure 12B:
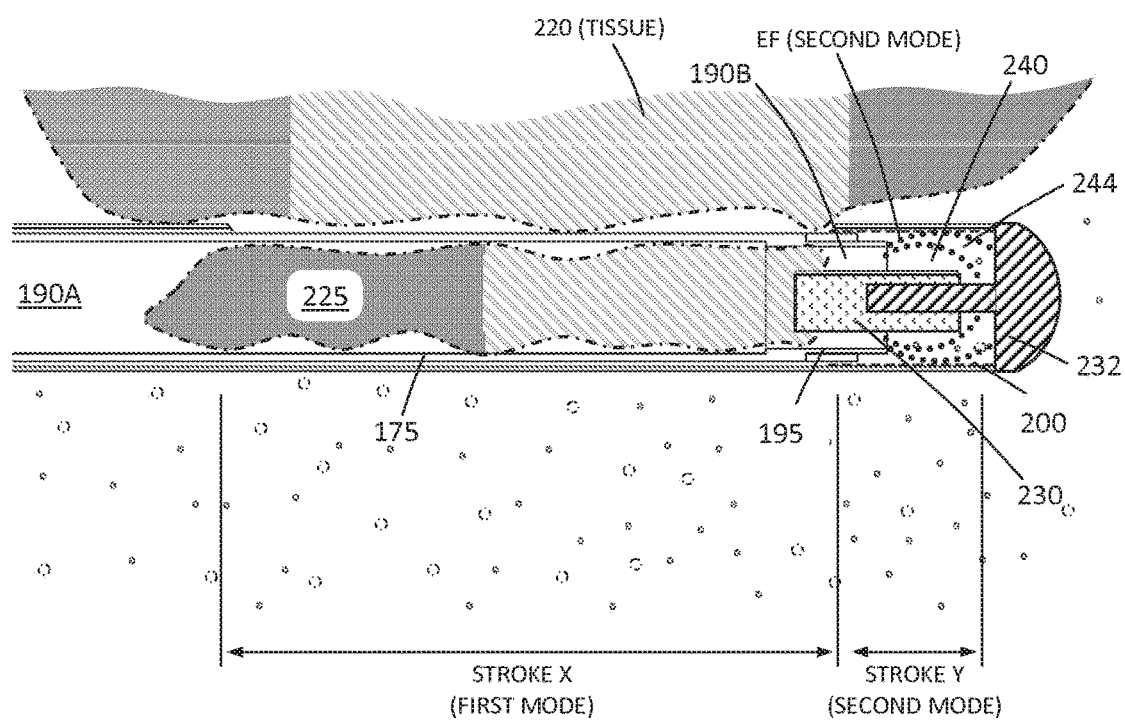
FIG. 12B is an enlarged sectional view of the working end of FIG. 11C with the reciprocating RF cutting sleeve almost fully extended and showing the RF fields switching to a second RF mode from a first RF mode shown in FIG. 12.
Figure 12C:
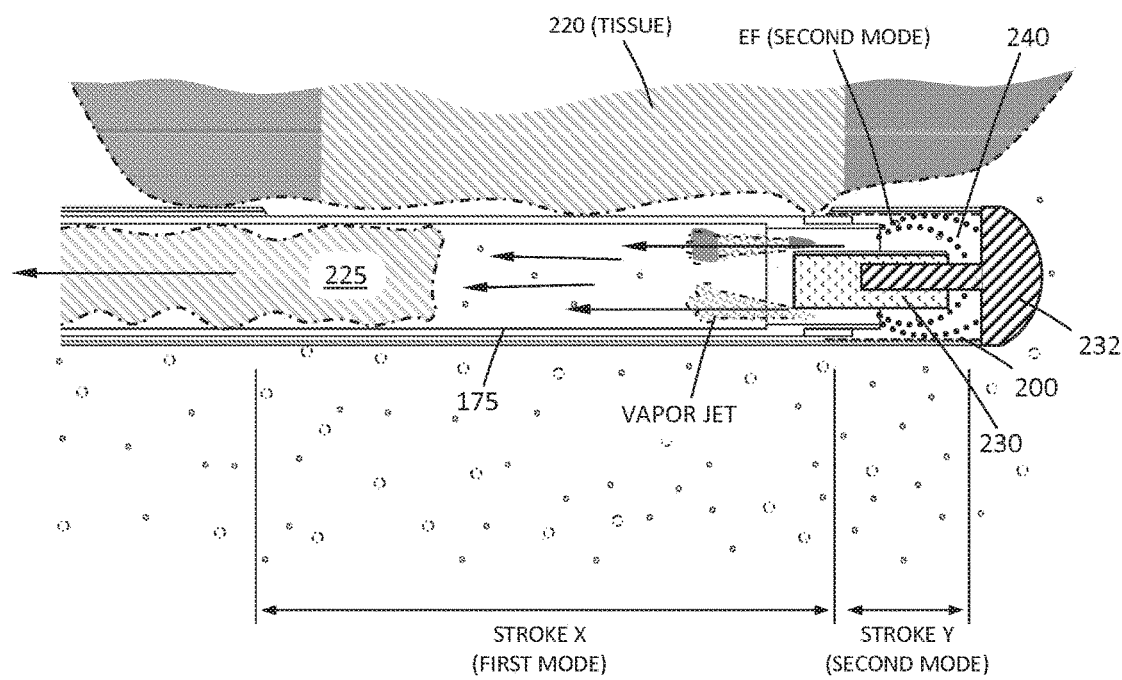
FIG. 12C is an enlarged sectional view of the working end of FIG. 11C with the reciprocating RF cutting sleeve again almost fully extended and showing the explosive vaporization of a captured liquid volume to expel cut tissue in the proximal direction.

More in particular, FIGS. 12A-12C illustrate sequentially the functional aspects of the tissue displacement mechanisms and the explosive vaporization of fluid captured in chamber 240. In FIG. 12A, the reciprocating cutting sleeve 175 is shown in a medial position advancing distally wherein plasma at the cutting electrode edge 180 is cutting a tissue strip 225 that is disposed within lumen 160 of the cutting sleeve 175. In FIG. 12A-12C, it can be seen that the system operates in first and second electrosurgical modes corresponding to the reciprocation and axial range of motion of cutting sleeve 175 relative to the tissue-receiving window 176. As used herein, the term "electrosurgical mode" refers to which electrode of the two opposing polarity electrodes functions as an "active electrode" and which electrode functions as a "return electrode". The terms "active electrode" and "return electrode" are used in accordance with convention in the art—wherein an active electrode has a smaller surface area than the return electrode which thus focuses RF energy density about such an active electrode. In the working end 145 of FIGS. 10A-11C, the cutting electrode element 195 and its cutting electrode edge 180 must comprise the active electrode to focus energy about the electrode to generate the plasma for tissue cutting. Such a high-intensity, energetic plasma at the electrode edge 180 is needed throughout stroke X indicated in FIG. 12A-12B to cut tissue. The first mode occurs over an axial length of travel of inner cutting sleeve 175 as it crosses the tissue-receiving window 176, at which time the entire exterior surface of outer sleeve 170 comprises the return electrode indicated at 185. The electrical fields EF of the first RF mode are indicated generally in FIG. 12A.

Figure 14:
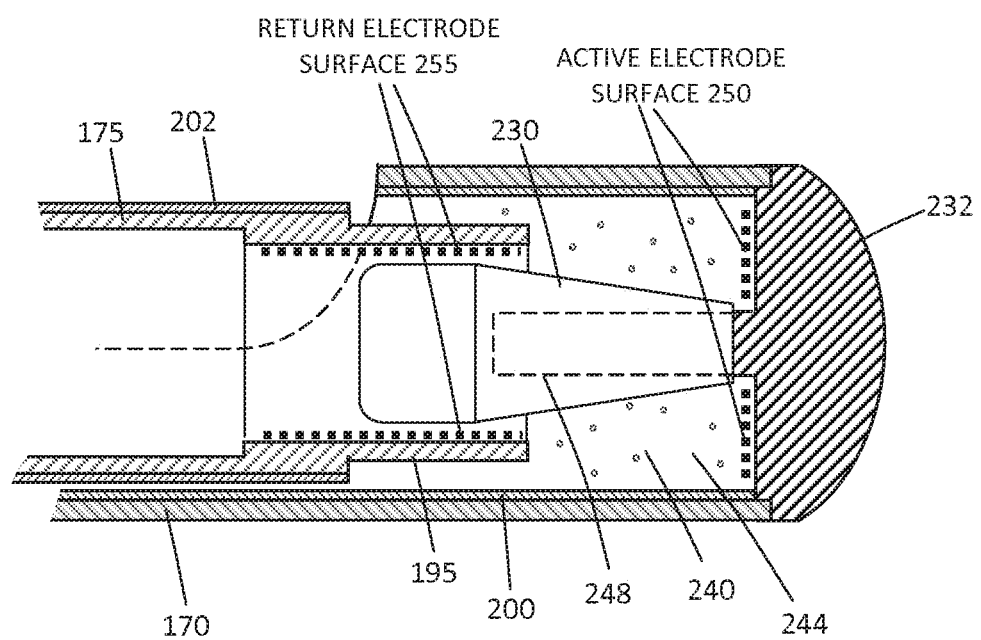
FIG. 14 is a sectional view of the working end of FIG. 12C showing an interior chamber and a variation of a projecting element.

FIG. 12 B illustrates the moment in time at which the distal advancement or extension of inner cutting sleeve 175 entirely crossed the tissue-receiving window 176. At this time, the electrode sleeve 195 and its electrode edge 180 are confined within the mostly insulated-wall chamber 240 defined by the outer sleeve 170 and distal tip 232. At this moment, the system is configured to switch to the second RF mode in which the electric fields EF switch from those described previously in the first RF mode. As can be seen in FIG. 12B, in this second mode, the limited interior surface area 250 of distal tip 232 that interfaces chamber 240 functions as an active electrode and the distal end portion of cutting sleeve 175 exposed to chamber 240 acts as a return electrode. In this mode, very high energy densities occur about surface 250 and such a contained electric field EF can explosively and instantly vaporize the fluid 244 captured in chamber 240. The expansion of water vapor can be dramatic and can thus apply tremendous mechanical forces and fluid pressure on the tissue strip 225 to move the tissue strip in the proximal direction in the tissue extraction lumen 160. FIG. 12C illustrates such explosive or expansive vaporization of the distention fluid 244 captured in chamber 240 and further shows the tissue strip 225 being expelled in the proximal direction the lumen 160 of inner cutting sleeve 175. FIG. 14 further shows the relative surface areas of the active and return electrodes at the extended range of motion of the cutting sleeve 175, again illustrating that the surface area of the non-insulated distal end surface 250 is small compared to surface 255 of electrode sleeve which comprises the return electrode.

Still referring to FIGS. 12A-12C, it has been found that a single power setting on the RF source 150 and controller 155 can be configured both (i) to create plasma at the electrode cutting edge 180 of electrode sleeve 195 to cut tissue in the first mode, and (ii) to explosively vaporize the captured distention fluid 244 in the second mode. Further, it has been found that the system can function with RF mode-switching automatically at suitable reciprocation rates ranging from 0.5 cycles per second to 8 or 10 cycles per second. In bench testing, it has been found that the tissue-cutting device described above can cut and extract tissue at the rate of from 4 grams/min to 8 grams/min without any potential for tissue strips 225 clogging the tissue-extraction lumen 160. In these embodiments, the negative pressure source 125 also is coupled to the tissue-extraction lumen 160 to assist in applying forces for tissue extraction.

Of particular interest, the fluid-capture chamber 240 defined by sleeve 170 and distal tip 232 can be designed to have a selected volume, exposed electrode surface area, length and geometry to optimize the application of expelling forces to resected tissue strips 225. In one embodiment, the diameter of the chamber is 3.175 mm and the length is 5.0 mm which taking into account the projecting element 230, provided a captured fluid volume of approximately 0.040 mL. In other variations, the captured fluid volume can range from 0.004 to 0.080 mL.

In one example, a chamber 240 with a captured liquid volume of 0.040 mL together with 100% conversion efficiency in and instantaneous vaporization would require 103 Joules to heat the liquid from room temperature to water vapor. In operation, since a Joule is a W*s, and the system reciprocate at 3 Hz, the power required would be on the order of 311 W for full, instantaneous conversion to water vapor. A corresponding theoretical expansion of 1700× would occur in the phase transition, which would results in up to 25,000 psi instantaneously (14.7 psi×1700), although due to losses in efficiency and non-instantaneous expansion, the actual pressures would be much less. In any event, the pressures are substantial and can apply significant expelling forces to the captured tissue strips 225.

Figure 13:
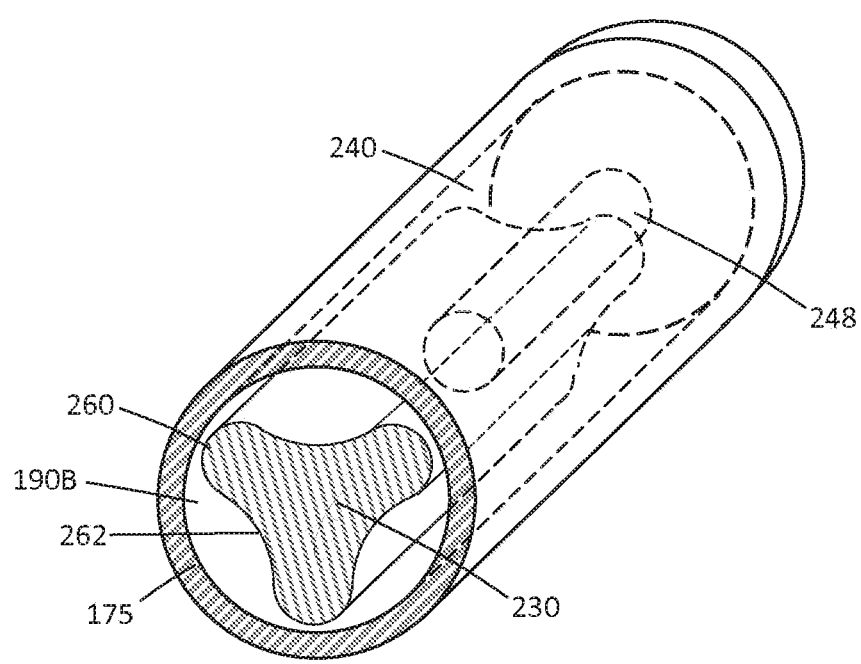
FIG. 13 is an enlarged perspective view of a portion of the working end of FIG. 12C showing an interior chamber and a fluted projecting element.

Referring to FIG. 12A, the interior chamber 240 can have an axial length from about 0.5 mm to 10 mm to capture a liquid volume ranging from about 0.004 mL 0.01 mL. It can be understood in FIG. 12A, that the interior wall of chamber 240 has an insulator layer 200 which thus limits the electrode surface area 250 exposed to chamber 240. In one embodiment, the distal tip 232 is stainless steel and is welded to outer sleeve 170. The post element 248 is welded to tip 232 or machined as a feature thereof. The projecting element 230 in this embodiment is a non-conductive ceramic. FIG. 13 shows the cross-section of the ceramic projecting element 230 which is fluted, which in one embodiment has three flute elements 260 in three corresponding axial grooves 262 in its surface. Any number of flutes, channels or the like is possible, for example from 2 to about 20. The purpose of this design is to provide a significant cross-sectional area at the proximal end of the projecting element 230 to push the tissue strip 225, while at the same time the three grooves 262 permit the proximally-directed jetting of water vapor to impact the tissue exposed to the grooves 262. In one embodiment, the axial length D of the projecting element 230 is configured to push tissue entirely out of the reduced cross-sectional region 190B of the electrode sleeve element 195. In another embodiment, the volume of the chamber 240 is configured to capture liquid that when explosively vaporized provided a gas (water vapor) volume sufficient to expand into and occupy at least the volume defined by a 10% of the total length of extraction channel 160 in the device, at least 20% of the extraction channel 160, at least 40% of the extraction channel 160, at least 60% of the extraction channel 160, at least 80% of the extraction channel 160 or at least 100% of the extraction channel 160.

As can be understood from FIGS. 12A to 12C, the distending fluid 244 in the working space replenishes the captured fluid in chamber 240 as the cutting sleeve 175 moves in the proximal direction or towards its non-extended position. Thus, when the cutting sleeve 175 again moves in the distal direction to cut tissue, the interior chamber 240 is filled with fluid 244 which is then again contained and is then available for explosive vaporization as described above when the cutting sleeve 175 closes the tissue-receiving window 176. In another embodiment, a one-way valve can be provided in the distal tip 232 to draw fluid directly into interior chamber 240 without the need for fluid to migrate through window 176.

Figure 15:
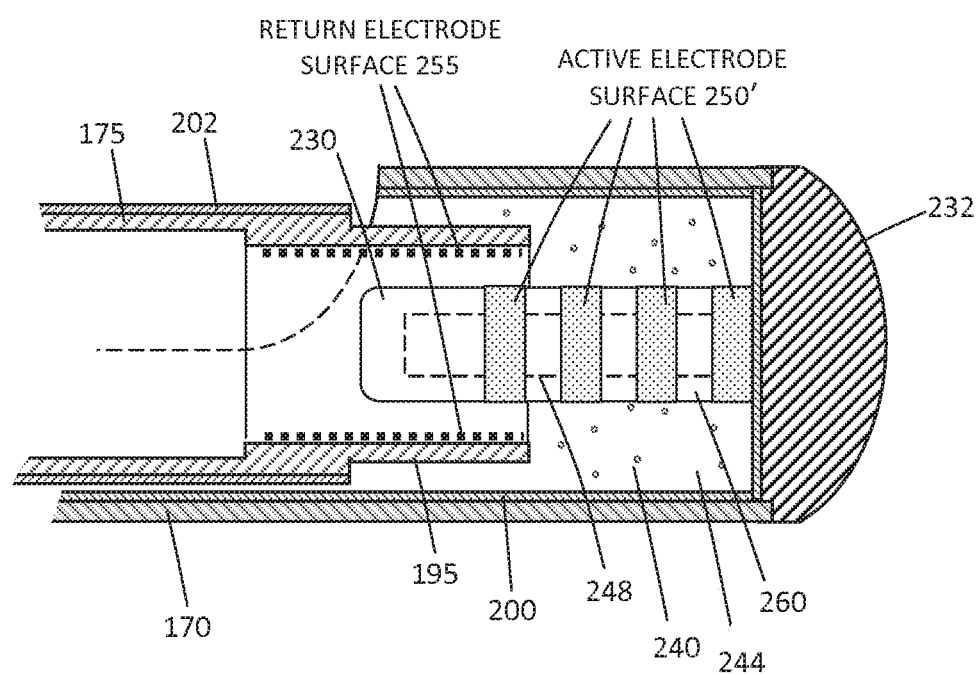
FIG. 15 is a sectional view of the working end of FIG. 12C showing an interior chamber and a variation of a projecting element configured to explosively vaporize the captured liquid volume.

FIG. 15 illustrates another variation in which the active electrode surface area 250' in the second mode comprises a projecting element 230 with conductive regions and non-conductive regions 260 which can have the effect of distributing the focused RF energy delivery over a plurality of discrete regions each in contact with the captured fluid 244. This configuration can more efficiently vaporize the captured fluid volume in chamber 240. In one embodiment, the conductive regions 250' can comprise metal discs or washers on post 248. In other variation (not shown) the conductive regions 250' can comprise holes, ports or pores in a ceramic material 260 fixed over an electrically conductive post 248.

In another embodiment, the RF source 150 and controller 155 can be programmed to modulate energy delivery parameters during stroke X and stroke Y in FIGS. 12A-12C to provide the optimal energy (i) for plasma cutting with electrode edge 180, and (ii) for explosively vaporizing the captured fluid in chamber 240.

It should be appreciated that while an RF source is suitable for causing explosive vaporization of the captured fluid volume, any other energy source can be used and falls within the scope of the invention, such as an ultrasound tranducer, HIFU, a laser or light energy source, a microwave or a resistive heat source.

In another embodiment, the probe can be configured with a lumen in communication with a remote liquid source to deliver fluid to the interior chamber 240.

Figure 16:
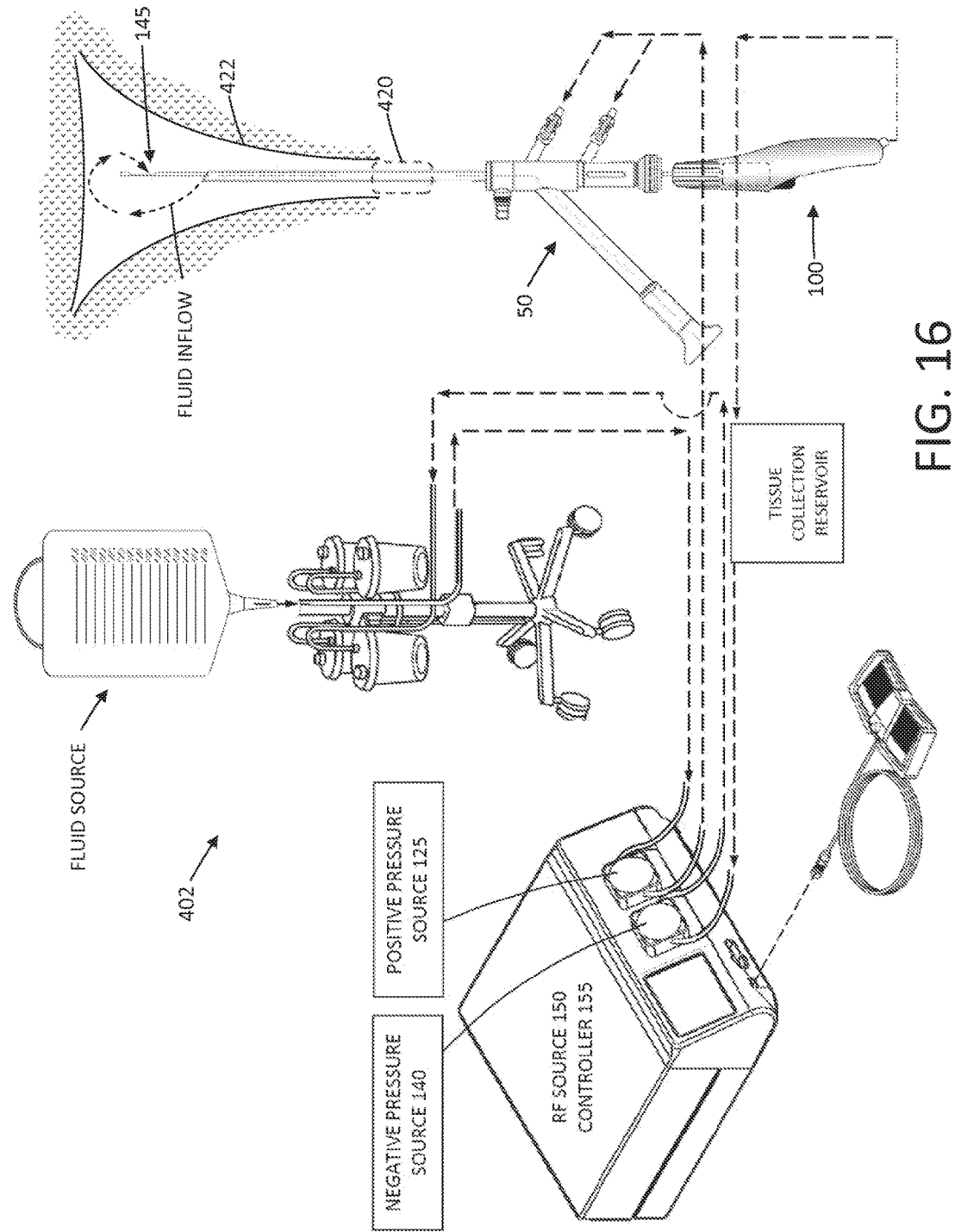
FIG. 16 is a schematic view of a system for fibroid removal including a fluid management system.
Figure 17:
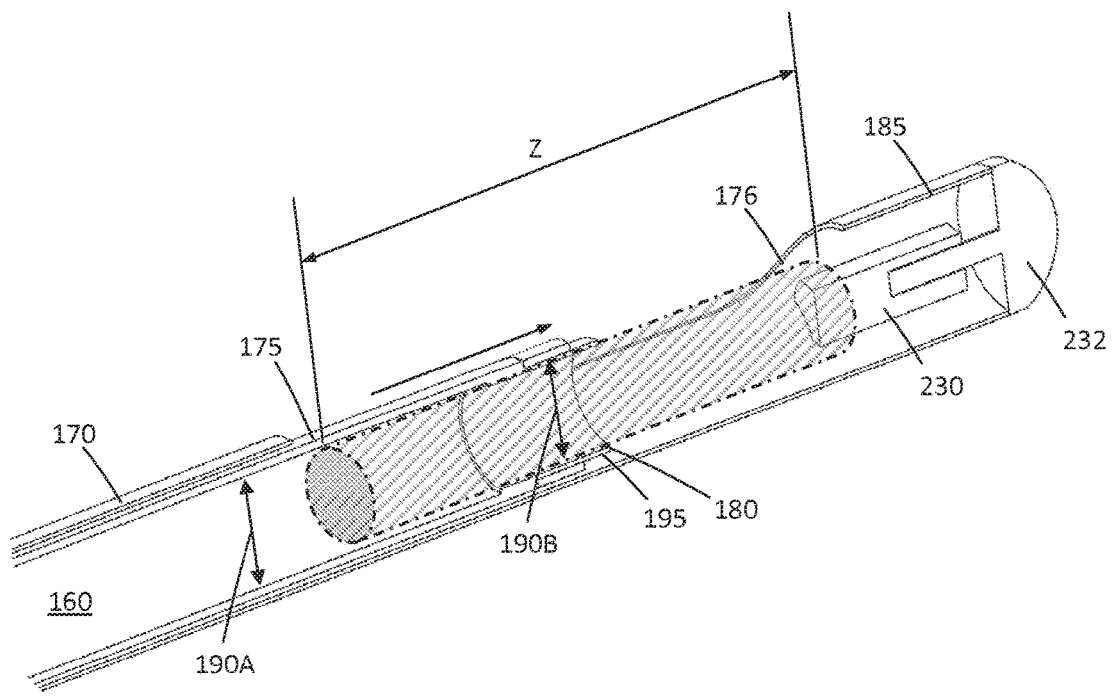
FIG. 17 is a longitudinal sectional view of a working end similar to that of FIGS. 11A-11C showing a maximum cut volume.

FIG. 16 illustrates an embodiment of a hysteroscopic system 400 for fibroid cutting and extraction that comprises a hysteroscope 50 and cutting tool 100 as describe above together with an integrated fluid management system 402. The fluid management system is integrated with controller 150 which controls the positive pressure source 125 and the negative pressure source 140 for controlling all inflows of distending fluid and outflows of distending fluid. It has been found that the probe 100 and internal RF cutting sleeve 175 can be extremely efficient in cutting tissue slugs or strips when engaging tissue under suitable slight contacting pressure. In use, the system can cut tissue on each extending stroke that can approximate the theoretical maximum "cut volume"—which term I used herein to describe the cylindrical tissue volume defined by the inner diameter of reduced cross section 190B of RF sleeve 195 and the length of the stroke (or longitudinal window dimension) and is depicted in FIG. 17. In other words, FIG. 17 illustrates the potential tissue volume that can be cut in a single extending stroke of the cutting sleeve 175. In one embodiment, the cut volume can comprise 55 $mm^3$ wherein the inner bore of lumen 190B is 0.85" and the window 176 is 15 mm in length Z. In other embodiments which still maintain the O.D. of the outer sleeve 170 at 0.145" or less, and by providing a larger lumen 190B, the cut volume can be at least 60 mm³, 65 mm³ or 70 mm³. The definition of cut volume does not separately distinguish the slight thickness of tissue that is cut by the RF plasma—which is vaporized altogether.

In actual operation, the efficiency has been found to be very high, wherein the efficiency is defined as the percentage of maximum cut volume that is cut per stroke. For example, the probe's efficiency can be 80%, 90% or 100% on each extending stroke after which the tissue is then extracted by means described above after extension of the cutting sleeve 175 past the window 176.

It can be easily understood that if the cutting efficiency is very high as described above, the reduced cross section lumen 190B and extraction lumen 160 will be substantially occupied by tissue during operation and thus leave little room for distending fluid to be extracted with the tissue strips or slugs. This aspect of the invention is highly advantageous as the risk of intravasation can be reduced, the fluid management system can be simplified and the fluid management system can be more compact and potential well-suited for office-based procedures instead of hospital operating rooms.

Referring to FIG. 16, in one system embodiment with lumen dimensions described above, if the system is left "open" with the ablation probe's working end 145 disposed in a sealed and distended cavity 405 (e.g. a uterine cavity) and the negative pressure source operated at a level of approximately 600 mmHg, when a suitable pressure is applied to distend the cavity—then a flow rate will range from about 550 mL/min to 700 mL/min flowing through the open system. In actual operation, it has been found that the efficiency of the RF cutting system can reduce the inflows to less 400 mL/min, less than 300 mL/min and as low as 200 mL/min. In this system, a cervical seal 420 is used to prevent leakage of distending fluid from the cavity 422.

In general, a method of the invention for cutting and extracting tissue from a body cavity comprises distending a body cavity with distending fluid inflow, cutting tissue with a reciprocating RF cutting sleeve configured to reciprocate and capture tissue strips in a distal portion of an extraction lumen of an elongate probe, extracting the tissue strips and distending fluid at least in part by applying negative pressure to the extraction lumen thereby causing a distending fluid outflow, and managing the fluid inflows and outflows with a controller to limit distending fluid inflows to less than 400 mL/min.

In such a method, the probe can have an extraction lumen 160 that has a mean diameter of at least 0.085", at least 0.090", at least 0.095" or at least 0.100", wherein the larger lumens obviously increase the difficulty in lowering fluid inflow rates. The method includes operating the RF cutting sleeve in a reciprocation range of 0.5 Hz to 4.0 Hz. The method allows the RF cutting sleeve to cuts tissue at the rate of at least 2 grams/min, at least 3 grams/min or at least 4 grams/min. In this method, the controller can further limit the fluid inflows to less than 300 mL/min, less than 250 mL/min or less than 200 mL/min.

In another variation for reducing the inflows of distending fluids, the controller 155 can modulates inflows and/or outflows depending on which portion or position of the stroke of the RF cutting sleeve 175. For example, the controller can use maximum suction for only a selected initial portion of the extending stroke (e.g., 20%, 30%, 40%, 50% or 60%) after which time the tissue that was suctioned into the window 176 will not have time to rebound outwardly before being cut. Further, when the sleeve 175 is in its retraction stroke, the negative pressure can be reduced since the movement of the sleeve itself is moving the tissue proximally in the extraction lumen 160. In another variation, the negative pressure can be pulsed.

In another variation for reducing the inflows of distending fluids into the body cavity, the controller 155 can modulate inflows and/or outflows in response to measured fluid pressure in the body cavity. The probe 100 can carry a pressure sensor, or pressure sensor can be introduced through the hysteroscope. In another variation, the controller can modulate inflows and/or outflows at least in part in response to a measured negative pressure in communication with the extraction lumen. In another method, the controller 155 can compare intracavity pressure and applied negative pressure and modulate either inflows or outflow negative pressure.

In general, a method of cutting and extracting tissue from a body cavity comprises distending a body cavity with distending fluid inflow, cutting tissue with a reciprocating RF cutting sleeve configured to reciprocate and capture tissue strips in a distal portion of an extraction lumen of an elongate probe, extracting the tissue strips and distending fluid at least in part by applying negative pressure to the extraction lumen thereby causing a distending fluid outflow, and modulating at least one of an inflow rate or an outflow rate in response to feedback from a sensor system. The sensor can be configured to measure pressure in the body cavity, to measure negative pressure coupled to the extraction lumen, or to compare pressure in the body cavity and the negative pressure coupled to the extraction lumen.

In another aspect of the invention, a method of cutting and extracting tissue from a body cavity comprises distending a body cavity with distending fluid inflow, cutting tissue with a reciprocating RF cutting sleeve configured to reciprocate and capture tissue strips in a distal portion of an extraction lumen of an elongate probe, extracting the tissue strips and distending fluid at least in part by applying negative pressure to the extraction lumen thereby causing a distending fluid outflow; and modulating at least one operational parameter in response to feedback signals from sensors coupled to a controller. The operational parameters can be selected from the group consisting of applied RF power, fluid inflow rate, fluid inflow pressure, reciprocation rate and negative pressure coupled to the extraction lumen. The feedback signals can be selected from the group consisting of impedance, capacitance of compositions in the extraction lumen, fluid pressure level in the body cavity, reciprocation rate and negative pressure level in the extraction lumen.

In another aspect of the invention, referring to FIG. 17, a medical system for cutting and extracting tissue form a body cavity comprises a probe comprising a windowed outer sleeve and a concentric inner RF cutting sleeve that defines a per stroke cutting volume of at least 50 mm³, and a fluid management system comprising a distending fluid source, a pump mechanism and a controller for controlling inflows and outflows of a distending fluid from the body cavity, wherein the fluid management system is configured to deliver a distension fluid volume of less than 400 mL/min, less than 300 mL/min or less than 200 mL/min. In another variation, the RF cutting sleeve defines a per stroke cutting volume of at least 55 mm³, 60 mm³, 65 mm³ or 70 mm³. The reciprocation of the RF cutting sleeve can be in the range of 0.5 Hz to 4.0 Hz.

In general, a medical system of the invention for cutting and extracting tissue form a body cavity comprises a probe comprising a windowed outer sleeve and a concentric inner RF cutting sleeve configured to cut tissue at a rate of at least 3 grams/min, and a fluid management system comprising a distending fluid source, a pump mechanism and a controller for controlling inflows and outflows of a distending fluid from the body cavity, wherein the fluid management system is configured to deliver a distension fluid volume of less than 400 mL/min, less than 300 mL/min or less than 200 mL/min.

Figure 18:
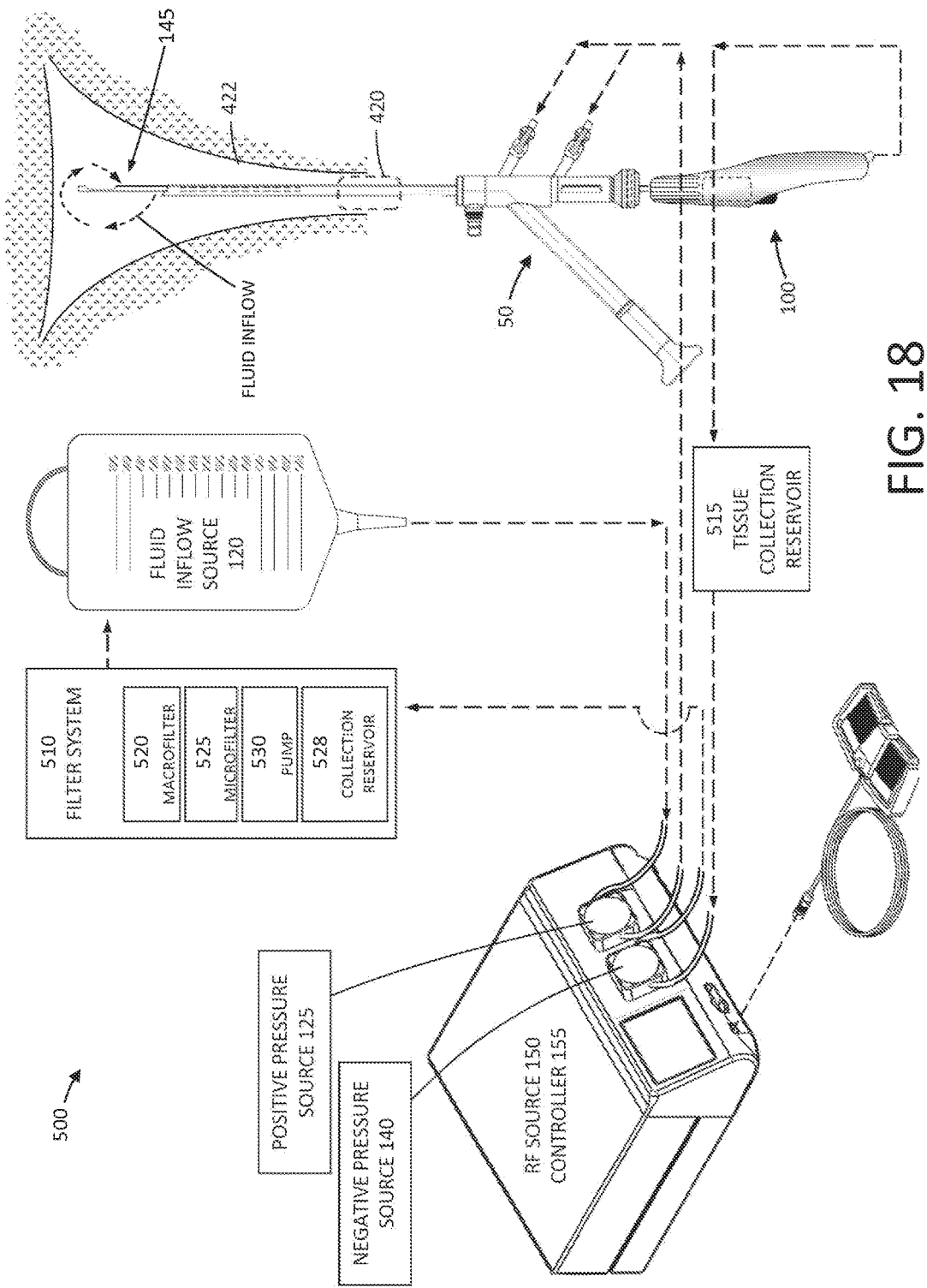
FIG. 18 is a schematic view of a fluid management system corresponding to the invention.
Figure 19:
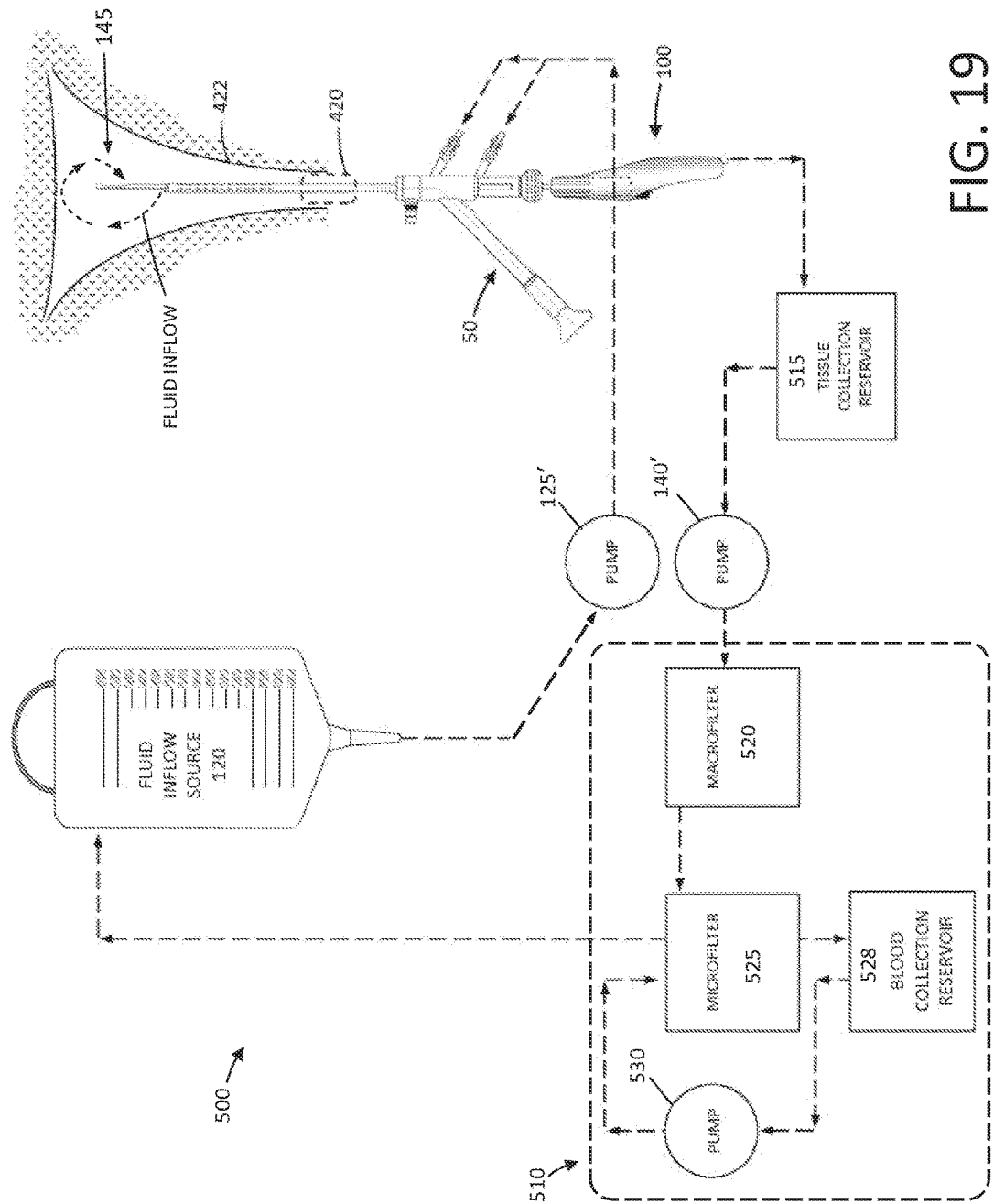
FIG. 19 is a box diagram showing various pump and filter components of the fluid management system of FIG. 18.

FIGS. 18-19 illustrate a fluid management system 500 that can be used when treating tissue in a body space, cavity or potential space, and is depicted schematically in a hysteroscopic system embodiment for cutting and extraction of fibroids or other abnormal intra-uterine tissue. A body cavity or uterine cavity 422 is shown with a cervical seal 420 positioned in the external cervical os and cervical canal. The fluid management system 500 again is integrated with a controller 155 that is configured to control the positive pressure source 125 (or pump 125') and the negative pressure source 140 (or pump 140') for controlling inflows of distending fluid from source 120 and outflows of such distending fluid. In this embodiment, a probe 100 is shown with the working end 145 disposed in the uterine cavity 422.

Referring to FIG. 18, in general, the fluid management system 500 of the invention comprises a source or container 120 of distending fluid, a pumping system for maintaining the distension of a body cavity, a filter system 510 for filtering distending fluid that is recovered from the body cavity and a further subsystem for returning the filtered fluid to the source 120. The use of such recovered and filtered fluid and the replenishment of the fluid supply 120 is advantageous because (i) the closed-loop fluid management system 500 system can effectively measure fluid deficit to thereby monitor intravasation to thereby insure patient safety, (ii) the system can be set up and operated in a much more time-efficient manner that prior art fluid deficit monitoring systems, and (ii) the system can be very compact and less expensive to enable office-based procedures.

FIG. 19 illustrates the fluid management system 500 in more detail wherein a first pump 125' provides an inflow of a distending fluid from fluid source 120 into the body cavity or potential space 422 at a suitable rate, e.g., ranging from 200 mL/min to 750 mL/min. The system has a second pump 140' to assist in removing and recovering fluid removed from space 422. A tissue collection reservoir 515 collects resected tissue strips. Thereafter, the recovered fluid is moved by pump 140' into the filter system 510. More in particular, the filter system 510 comprises a first filter 520 or macrofilter that accommodates high flows from about 200 mL/min to 2000 mL/min and is adapted for removing cells and particulate matter from the fluid flow. In one variation, the first filter 520 has pore size of about 10 microns, 5 microns or 1 micron. As can be seen in FIG. 19, the second filter or microfilter 525 is a low volume filter for use in ultra-filtration of fluids as is known in the art and is adapted for the removal of molecules having a weight greater than 100 kD or 50 kD. The debris or blood constituents filtered from the microfilter is collected in blood collection reservoir 528 (FIG. 19). In one variation, a pump 530 is provided for a looped flow through the microfilter 525 to cleanse the distending fluid for subsequent return to the fluid source or container 120.

In general, the fluid management system 500 corresponding to the invention comprises a first pump for providing an inflow of a distending fluid from fluid source 120 to the body cavity or potential space, a second pump for removing and recovering fluid removed from the space and a controller and filter system for filtering recovered fluid and thereafter re-circulating the filtered fluid to the fluid source 120.

In one embodiment, the fluid management system 500 has a controller configured for operation in a pressure control mode wherein the first and second pumps cooperate to deliver fluid to the space or cavity 422 (FIGS. 18-19) and maintain pressure therein within a predetermined pressure range. In another variation, the fluid management system has a controller configured for operation in a flow control mode wherein the first and second pumps cooperate to deliver fluid to the space within a predetermined flow rate range.

The fluid management system 500 of FIGS. 18-19 can utilize at least one pressure sensor capable of providing a pressure signal indicating fluid pressure in the space 422 to enable or assist in operating in various modes, for example, the pressure mode or the flow control mode. The pressure sensor can be disposed in an inflow lumen that delivers the distending fluid inflow. In another variation, the pressure sensor can be disposed in a lumen that receives the distending fluid outflow.

In one embodiment, the fluid management system has a controller 155 configured for calculation of a fluid deficit that is measured as a difference between a fluid volume delivered to the space 422 and a fluid volume recovered from the space (see FIG. 18). The controller 155 can be configured to compare pressure signals from at least two pressure sensors, wherein the controller is further configured to terminate or stop the pump if two pressure signals differ by a predetermined minimum amount.

In another embodiment, the fluid management system includes a disposable tubing set for delivering fluid to a probe or hysteroscope introduced into the space 422, wherein the tubing set includes at least one pulse dampener for use with a peristaltic or other pump (not shown).

In another aspect of the invention, a method of monitoring a fluid deficit is provided in the use of a fluid management system in a treatment in a body space which comprises (i) recording an initial reference volume comprising a volume of distending fluid contained within a supply container, a system capacity volume, and a volume of the space, (ii) inflowing distending fluid into the space, recovering a fluid volume in an outflow from the space and re-circulating the recovered fluid to the supply container to provide a replenished volume, and (iii) calculating the fluid deficit by subtracting the replenished volume from the initial reference volume. The recording step can include priming a supply tubing set and a surgical device with the distending fluid. In another variation, the recording step includes inflowing distending fluid into the body space 422, and/or calculating the volume of the body space by imaging means. The method can further comprises sealing an access to the body space 422 to prevent the loss of distending fluid into the environment, such as in the use of a cervical seal. In another variation, the method can capture fluid loss through the access to the body space, measure such lost fluid volume, and calculate the fluid deficit taking into account the lost fluid volume. A user interface is provided in the controller 15 to monitor and signal one or more fluid deficit parameters on an intermittent or continuous basis—wherein the signal can be at least one of visual, aural and tactile.

Referring again to FIG. 18, a method of using a fluid management system in a treatment in a body cavity comprises actuating a first pump to deliver a distending fluid volume from a fluid source into the cavity, actuating a second pump to remove and recover fluid from the cavity, filtering the recovered fluid and re-circulating filtered fluid to the fluid source. The controller is adapted to operate in a first mode for maintaining distension of the cavity wherein fluid pressure is maintained in the cavity 422 in a predetermined range. In one variation, the predetermined range is between 20 mmHg and 200 mmHg. In another method, the controller operates in second mode configured to maintain an inflow rate in a predetermined range, wherein the range is between 200 mL/min and 1000 mL/min. In one variation, the filtering step includes flowing the recovered fluid through a first filter mechanism to remove matter having mean cross section of 1 micron and larger. The filtering step further includes flowing the recovered fluid through at least a second filter mechanism to remove molecules having a weight greater than 50 kD. A pump 530 can be provided to generate a pressure of at least 10 psi, 20 psi, 30 psi or 40 psi for re-circulating a portion of the fluid outflow through the at least one second filter mechanism. In one variation, the system can return filtered fluid to the distending fluid source 120 with a fluid recovery rate of at least 400 mL/min, 500 mL/min, 600 mL/min, 700 mL/min or 800 mL/min.

In one embodiment, the fluid management system 500 of FIG. 18 comprises a first pump for delivering a distending fluid to a body space through a probe, a second pump for providing fluid outflows from the space through a probe extraction lumen, and a controller operatively connected to the first and second pumps and the probe wherein the controller is configured to modulate the pumps to maintain a fluid pressure in the space in response to an indicator signal that indicates the extraction lumen is in an open, partly open or closed configuration. In this embodiment, the probe includes a windowed outer sleeve and a concentric reciprocating inner cutting sleeve wherein reciprocation of the cutting sleeve adjusts the extraction lumen between the open, partly open or closed configurations. Thus, the controller can reduce needed flows through the system by reducing at least one flow pressure (at pump 125' or 140' in FIG. 19) when the window is open and increasing at least one flow pressure when the window is closed. In another variation, the flow from either pump 125' or 140' can be pulsed.

In another variation of fluid management system, the system can comprise at least one pump for delivering a distending fluid to a body space through a probe and for providing fluid outflows from the space through a probe extraction lumen, wherein the probe comprises a windowed outer sleeve 170 and a reciprocating inner cutting sleeve 175 (FIGS. 11A-11C) wherein such reciprocation moves the probe between window-open and window-closed configurations and wherein a window-closing mechanism is provided to move the probe to the window-closed configuration in response to idling the reciprocation. This system will assist in maintaining distension of the body cavity while at the same time reducing the total volume of new fluid used in a procedure. In another variation, the window-closing mechanism includes a stroke sensing mechanism operatively connected to the cutting sleeve 175 for determining the stage of a reciprocating stroke of the cutting sleeve.

Figure 20:
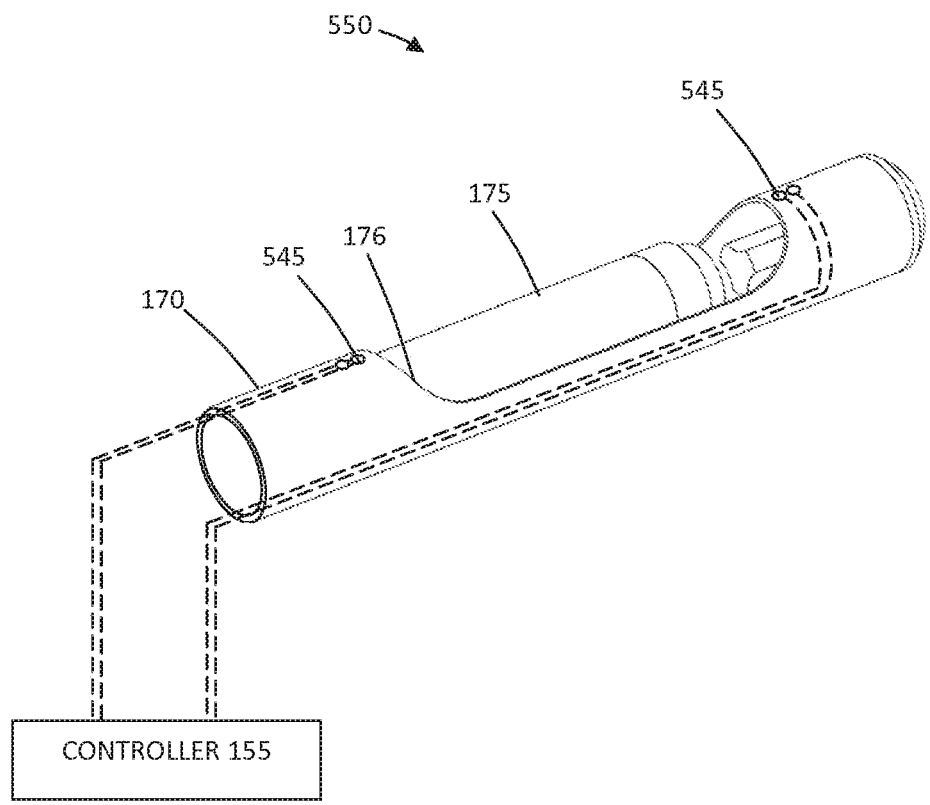
FIG. 20 is a view of the distal end of a cutting probe showing an electrical sensor for sensing tissue contact coupled to a controller of a fluid management system as in FIG. 18.

In another variation, the probe working end comprises a windowed outer sleeve and a reciprocating inner cutting sleeve wherein such reciprocation moves the probe between window-open and window-closed configurations and a controller and sensor system configured to signal if the probe working end is engaging tissue, and a controller algorithm configured to modulate the at least one pump in response to the signal. In one variation shown in FIG. 20, the sensor system comprises at least one capacitance sensor 545 at the edge of the window 176 on sleeve 170 which can measure a change in capacitance and compare capacitance against a stored library of values to determine whether the working end 550 is engaging tissue or is only submersed in the distending fluid. In response to the signal, the fluid management system can modulate and/or reduce flow pressures when the working end is not engaging and cutting tissue. In another variation, the capacitance sensor(s) could be positioned on the cutting sleeve 175. In other embodiments, the sensor system can be configured to function as described above, wherein the sensor system can be configured to measure impedance associated with at RF cutting sleeve, can be configured to measure pressure of compare pressures, or can be configured to measure loads on the cutting sleeve with a load sensor.

FIGS. 21-24 illustrate other embodiments of working ends that carry a second energy applicator surface, in addition to the electrode edge 180 described above. The second energy applicator surface is disposed about a distal superior surface of cutting sleeve 175 wherein such a surface is adapted to coagulate a tissue surface that was just cut by the electrode edge 180.

Figure 21:
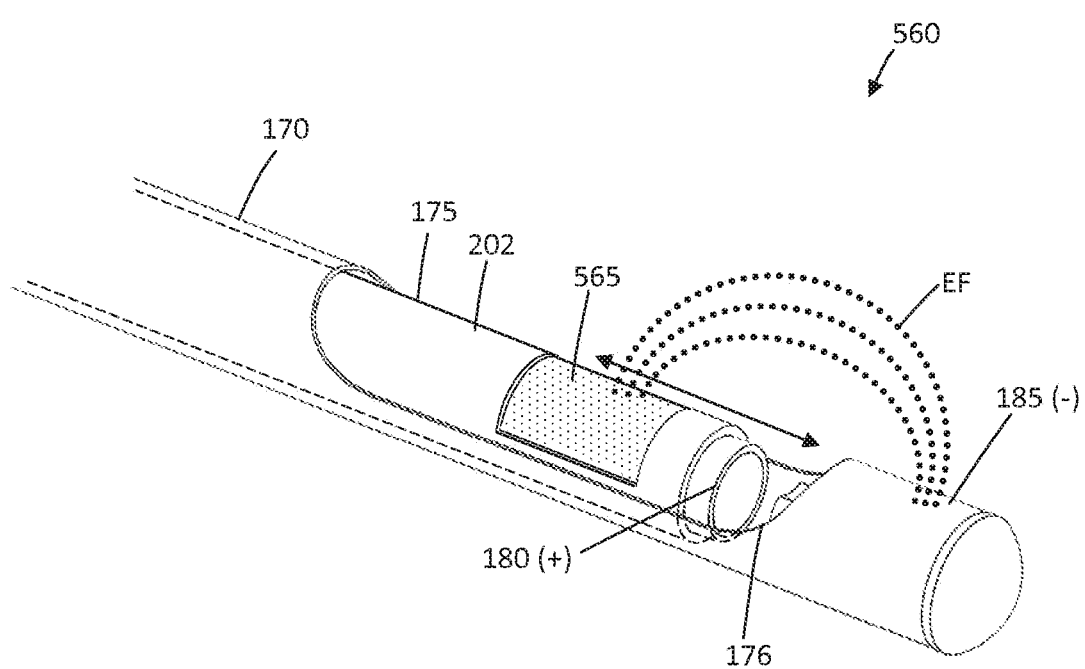
FIG. 21 is a view of the distal end of a cutting probe showing an energy applicator surface for tissue coagulation that functions contemporaneously with tissue cutting by the RF cutting sleeve.

In general, referring to FIG. 21, a method of resecting tissue corresponding to a probe of the invention comprises interfacing such an electrosurgical probe 560 with tissue targeted for resection, the probe comprising a cutting member configured to apply simultaneous first and second RF-induced energy application levels to tissue utilizing a single RF power mode, and moving the probe relative to tissue wherein (i) a leading portion (electrode 180) of the cutting member 175 applies a first energy level for vaporization and cutting of tissue and (ii) a trailing portion of the cutting member applies a second energy level for coagulating tissue. The probe comprises a windowed outer sleeve 170 and the cutting member 175 is reciprocatable therein across the window 176 to cut and coagulate tissue. As described above, the method provides a first RF-induced energy application level that generates plasma capable of vaporization and cutting of tissue. In the embodiment of FIG. 21, the method applies the second RF-induced energy from capacitive coupling through a thin-wall dielectric indicated at 565. The distal portion of the inner sleeve that is configured with the dielectric can extend from about 90° to 360° about a longitudinal axis of said sleeve. The dielectric can extend over a surface area of the inner sleeve 175 ranging between 1 mm$^2$ and 200 mm$^2$.

Figure 22:
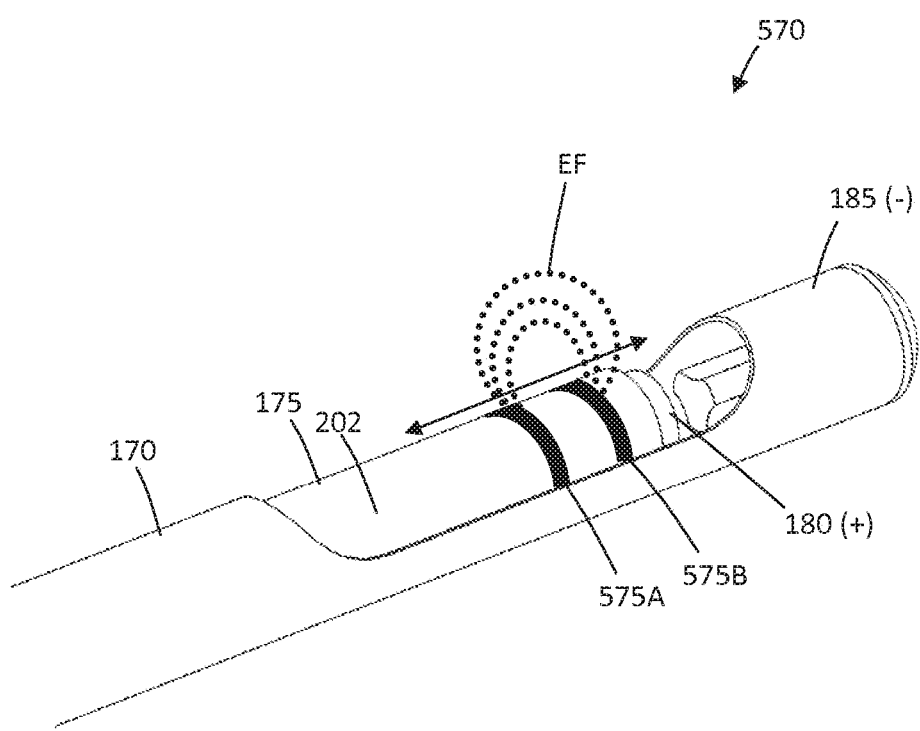
FIG. 22 is a view of the distal end of an alternative cutting probe.

FIG. 22 illustrates a probe working end 570 wherein the inner sleeve carries spaced apart opposing polarity electrodes 575A and 575B for delivering coagulation energy to tissue. These electrodes can be powered by the same RF source that delivers energy to the cutting electrode edge 180 or the RF sources for each energy applicator can be independent. The electric field is indicated at EF as if in contact with tissue.

Figure 24:
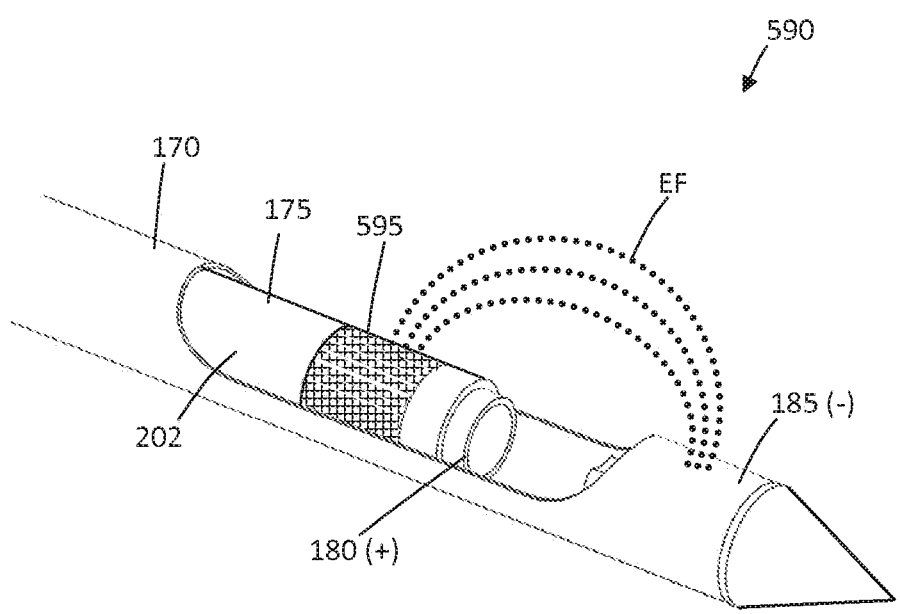
FIG. 24 is a view of the distal end of an alternative cutting probe.

FIG. 24 illustrates a probe working end 590 in which the inner cutting sleeve carries a positive temperature coefficient of resistance (PTCR) material 595 which can be designed to heat to a constant temperature for delivering coagulation energy to just-cut tissue. In another variation, the inner sleeve can be configured with a second RF applicator region that comprises any resistive material coupled to an electrical source.

In one aspect, referring to FIGS. 21-24, a tissue cutting probe consists of an elongated assembly comprising a windowed outer sleeve and a reciprocating inner cutting sleeve wherein such reciprocation moves the probe between window-open and window-closed configurations, wherein the inner cutting sleeve is configured with first and second discrete RF applicator regions, with both regions coupled to a single RF source. Further, the single RF mode operatively coupled to the sleeve (i) generates an ablative plasma at a tissue interface with the first RF applicator region for cutting tissue and (ii) causes tissue heating at a tissue interface with the second RF applicator region for coagulating a tissue surface. Typically, the first RF applicator region comprises a first polarity active electrode cooperating with a second polarity electrode having a larger surface area that said first polarity active electrode.

Figure 23:
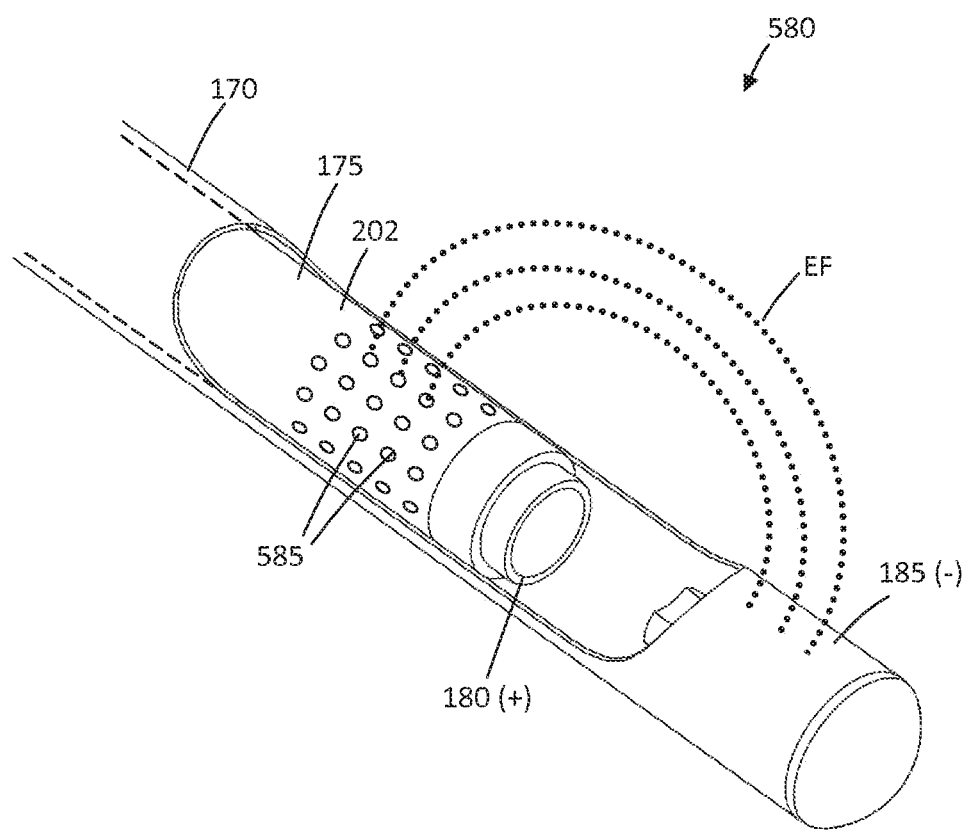
FIG. 23 is a view of the distal end of an alternative cutting probe.

In another embodiment depicted in FIG. 23, the second RF-induced energy can provide a low-intensity plasma for heating tissue. In FIG. 23, the first RF-induced energy application is provided at sharp distal end or edge 180 of the cutting member and the second RF-induced energy application is provided about a surface of the cutting member. The plasma can form in a plurality of pores or perforations 585 in the insulative layer 202 on the inner sleeve, with the pore ranging in cross section between about 10 microns and 1 mm. In this variation, a method of resecting tissue comprises interfacing an electrosurgical probe with tissue targeted for resection, the probe comprising a windowed outer sleeve and an reciprocating inner cutting sleeve with first and second RF applicator regions coupled to an RF source, and reciprocating the inner sleeve wherein a single RF mode applies an vaporizing plasma at the first RF applicator region for cutting tissue and applies non-vaporizing plasma at the second RF applicator region for coagulating a just-cut tissue surface.

In any embodiment described above, the inner cutting sleeve 175 can be configured to reciprocate in an extending stroke and a retracting stroke across the window wherein the application of the ablative plasma occurs only during the extending stroke, or during both strokes. The application of energy for coagulation purposes also can be limited to any portion of any stroke or can be continuous.

Figure 27:
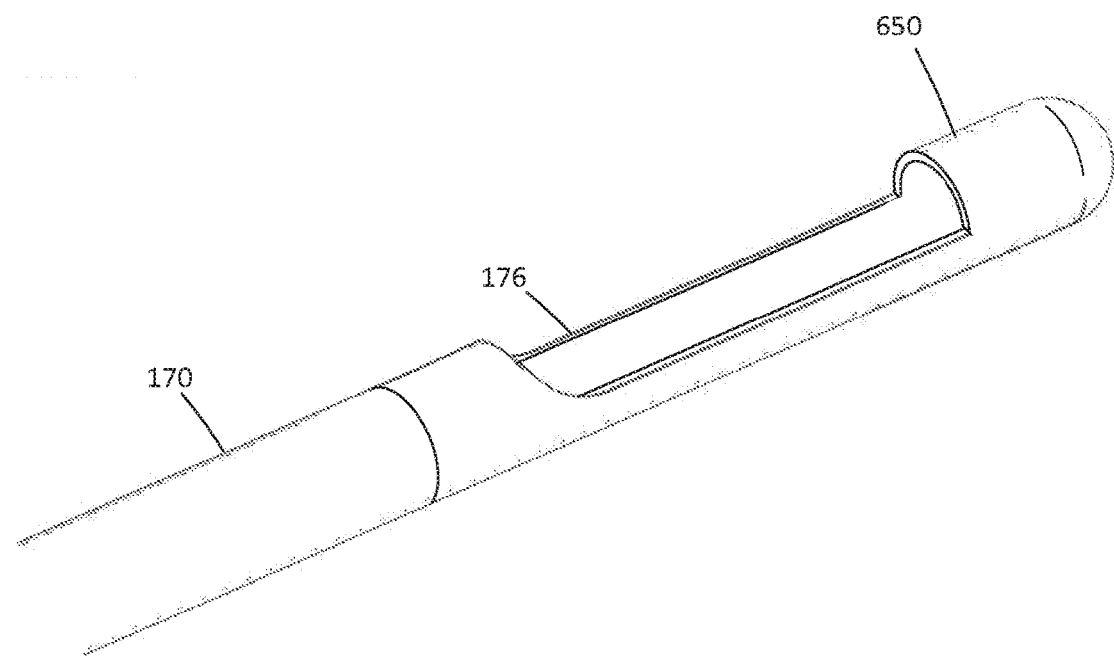
FIG. 27 is a view of the distal end of an alternative cutting probe wherein the distal body is a ceramic or other insulative material.

In another embodiment shown in FIG. 27, the probe can have an outer sleeve 170 with a distal body 650 that comprises a non-conductive material which comprise at least one of a ceramic, a glass or a polymer. It has been found that a dielectric or non-conductive material formed around window 176 or forming substantially the entirely of the distal end of the sleeve is useful for preventing the potential of shorting or arcing as the cutting sleeve 175 reciprocates in the bore in the outer sleeve.

In one variation of a probe with such a non-conductive distal body portion, the tissue cutting probe comprises an outer sleeve with a tissue-receiving window and a reciprocating inner cutting sleeve wherein such reciprocation moves the probe between window-open and window-closed configurations. An RF electrode is disposed at a distal edge of the cutting sleeve 175 and is coupled to an energy source wherein at least a surface of the outer sleeve proximate to the window is a material having a comparative tracking index value ranging from 200 volts to 800 volts.

In another aspect of the invention, referring to FIG. 24, the tissue cutting probe can have an outer sleeve configured with a cutting tip for penetrating tissue. The cutting tip can comprise a sharp tip or an RF tip. Any form of RF tip or sharp tip can be retractable.

Figure 25:
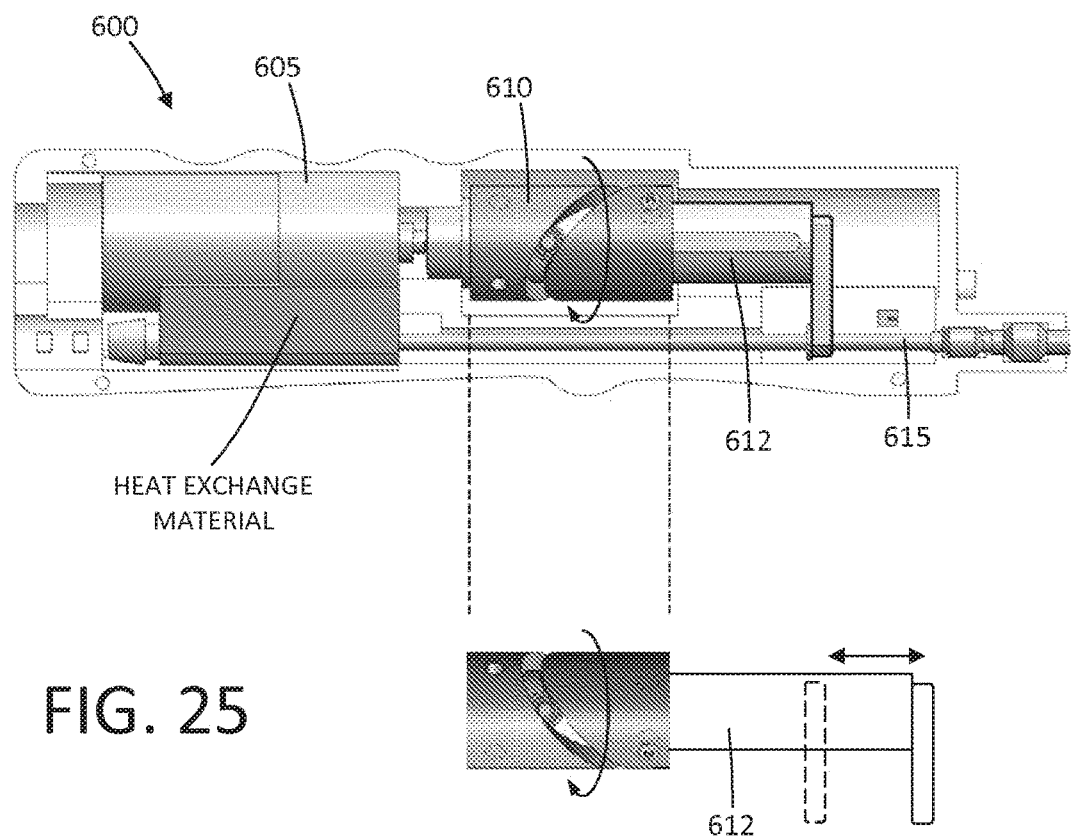
FIG. 25 is a schematic view of a handle of a tissue cutting probe.

In another aspect of the invention, referring to FIG. 25, the tissue cutting probe can have a motor drive in a handle 600 for reciprocating the cutting sleeve and a negative pressure source in communication with a tissue extraction channel in the inner sleeve. The tissue extraction channel can extends through the handle and include a heat exchanger configured to allow extracted fluids to cool the motor and/or handle.

Figure 26:
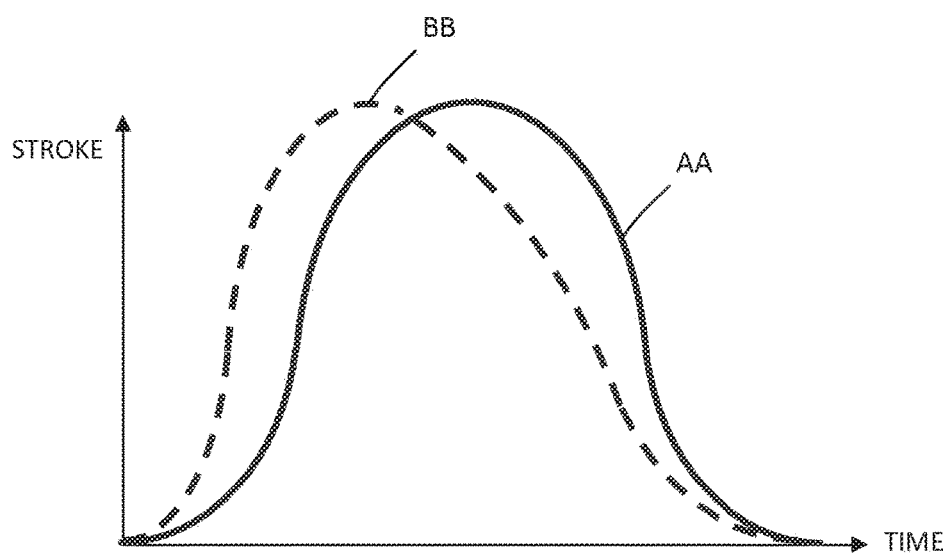
FIG. 26 is a graph showing variable reciprocation rates of a cutting sleeve.

In another aspect of the invention, referring to FIGS. 25-26, it can be seen that a motor drive 605 rotates actuator body 610 with an arcuate slot therein which engages a pin which in turn reciprocates shaft 612 and inner sleeve 615. It can be understood from FIGS. 25 and 26, that the shape of the arcuate slot in actuator body 610 can be varied to provide a variable reciprocation speed over the extending stroke and/or the retracing stroke, thus varying the reciprocation speed within one full reciprocation stroke of the inner reciprocating sleeve 615 independent of changing rotational speed of the motor drive 605, as depicted in stroke rates of speed AA and BB in FIG. 26. In one variation, the cutting sleeve can be configured with a faster speed on a retracting stroke and a slower speed during an extending stroke to increase RF cutting time when engaging tissue. In another variation, the cutting sleeve can have a dwell time in the fully extended stroke position to thereby allow negative and/or positive pressures to move tissue in the extraction lumen. In one variation, the cutting sleeve can have such a dwell time of at least 0.1 second. In another variation, the cutting sleeve can have a selectable peak speed range from 50 mm/s to 200 mm/s. A controller can be configured to allow such selectable reciprocation rates between 1 Hz and 4 Hz.

In another embodiment, the controller can move the cutting sleeve to the window-closed position when the motor is off. In another embodiment, the controller can be configured for the selection of a single extending stroke. In another embodiment, the controller can be configured for the selection of a single retraction stroke and locking the cutting sleeve in the window open position. In another embodiment, the controller can be configured for the selection of locking the cutting sleeve in a partially extended position.

In another embodiment, the controller can provide for the selection of a low RF power delivery with the cutting sleeve in a partially extended position for use in tissue coagulation.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:
1. A tissue resecting device comprising:
a handle;
an elongate shaft extending from the handle, the elongate shaft including an outer sleeve and a reciprocating inner resecting sleeve disposed in the outer sleeve, wherein such reciprocation of the inner resecting sleeve moves a distal end of the inner resecting sleeve across a tissue-receiving window of the outer sleeve between window-open and window-closed positions at a reciprocation speed;
a motor drive in the handle; and
an actuator in the handle coupled between the motor drive and the inner resecting sleeve to convert rotational motion from the motor drive to reciprocation motion of the inner resecting sleeve relative to the outer sleeve for reciprocating the inner resecting sleeve at the reciprocation speed, wherein the actuator is configured to vary the reciprocation speed within one full reciprocation stroke of the inner reciprocating sleeve independent of changing rotational speed of the motor drive;

wherein the actuator includes an actuator body with an arcuate slot therein, wherein rotational motion from the motor drive rotates the actuator body; and wherein the inner resecting sleeve extends proximal of the actuator body and reciprocates relative thereto.

2. The tissue resecting device of claim 1, wherein the full reciprocation stroke includes an extending stroke in which the inner resecting sleeve moves from the window-open position to the window-closed position and a retracting stroke in which the inner resecting sleeve moves from the window-open position to the window-closed position.

3. The tissue resecting device of claim 2, wherein the inner resecting sleeve has a faster speed during the retracting stroke and a slower speed during the extending stroke.

4. The tissue resecting device of claim 2, wherein the inner resecting sleeve has a dwell time in a fully extended stroke position to thereby allow negative and/or positive pressures to move tissue through the inner resecting sleeve.

5. The tissue resecting device of claim 4, wherein the dwell time is at least 0.1 second.

6. The tissue resecting device of claim 1, further comprising a controller for controlling reciprocation of the inner resecting sleeve.

7. The tissue resecting device of claim 6, wherein the controller is configured for locking the inner resecting sleeve in a partially extended position between the window-open position and the window-closed position.

8. The tissue resecting device of claim 6, wherein the controller is configured for locking the inner resecting sleeve in the window-open position.

9. The tissue resecting device of claim 6, wherein the controller is configured for locking the inner resecting sleeve in the window-closed position.

10. The tissue resecting device of claim 6, wherein a distal end of the inner resecting sleeve includes an RF electrode having a first polarity and the outer sleeve serves as a return electrode having an opposite, second polarity.

11. The tissue resecting device of claim 10, wherein the RF electrode is configured to generate plasma for resecting tissue.

* * * * *